US012631639B2

(12) United States Patent
Endell et al.

(10) Patent No.: US 12,631,639 B2
(45) Date of Patent: May 19, 2026

(54) METHODS FOR PREDICTING THERAPEUTIC BENEFIT OF ANTI-CD19 THERAPY IN PATIENTS

(71) Applicant: Incyte Corporation, Wilmington, DE (US)

(72) Inventors: Jan Endell, Munich (DE); Mark Winderlich, Munich (DE); Rainer Boxhammer, Aying (DE)

(73) Assignee: Incyte Corporation, Wilmington, DE (US)

( * ) Notice: Subject to any disclaimer, the term of this patent is extended or adjusted under 35 U.S.C. 154(b) by 703 days.

(21) Appl. No.: 17/824,266

(22) Filed: May 25, 2022

(65) Prior Publication Data

US 2022/0283166 A1 Sep. 8, 2022

Related U.S. Application Data

(63) Continuation of application No. 16/305,482, filed as application No. PCT/EP2017/063045 on May 30, 2017, now abandoned.

(30) Foreign Application Priority Data

May 30, 2016 (EP) ..................................... 16171885

(51) Int. Cl.
| | |
|---|---|
| *G01N 33/574* | (2006.01) |
| *A61K 39/395* | (2006.01) |
| *A61P 35/02* | (2006.01) |
| *A61P 35/04* | (2006.01) |
| *C07K 16/28* | (2006.01) |
| *A61K 39/00* | (2006.01) |

(52) U.S. Cl.
CPC ........ *G01N 33/57426* (2013.01); *A61P 35/02* (2018.01); *A61P 35/04* (2018.01); *C07K 16/2896* (2013.01); *G01N 33/57492* (2013.01); *A61K 39/395* (2013.01); *A61K 2039/505* (2013.01); *G01N 2333/70535* (2013.01); *G01N 2800/52* (2013.01)

(58) Field of Classification Search
CPC ..... G01N 2333/70535; G01N 2800/52; G01N 33/57426; G01N 33/57492; A61K 39/395; A61P 35/02; A61P 35/04; C07K 16/2896
See application file for complete search history.

(56) References Cited

U.S. PATENT DOCUMENTS

| | | | |
|---|---|---|---|
| 5,641,870 A | 6/1997 | Rinderknecht et al. | |
| 6,455,043 B1 * | 9/2002 | Grillo-Lopez .......... | A61P 37/00 424/1.49 |
| 6,703,199 B1 | 3/2004 | Koide | |
| 7,109,304 B2 | 9/2006 | Hansen et al. | |
| 8,097,703 B2 | 1/2012 | Rao-Naik et al. | |

| | | | |
|---|---|---|---|
| 8,546,399 B2 | 10/2013 | Bruncko et al. | |
| 9,174,982 B2 | 11/2015 | Bruncko et al. | |
| 11,224,654 B2 | 1/2022 | Endell et al. | |
| 12,194,095 B2 | 1/2025 | Endell et al. | |
| 2006/0233791 A1 | 10/2006 | Tedder et al. | |
| 2007/0154473 A1 | 7/2007 | Super et al. | |
| 2010/0167315 A1 | 7/2010 | Thibault et al. | |
| 2010/0272723 A1 | 10/2010 | Bernett et al. | |
| 2011/0052489 A1 | 3/2011 | Hansen et al. | |
| 2011/0312088 A1 | 12/2011 | McDonagh et al. | |
| 2012/0082664 A1 | 4/2012 | Bernett et al. | |
| 2013/0115657 A1 | 5/2013 | Damschroder et al. | |
| 2013/0273032 A1 | 10/2013 | Gerdes et al. ............. | 424/133.1 |
| 2014/0286934 A1 | 9/2014 | Blein et al. | |
| 2014/0288288 A1 | 9/2014 | Super et al. | |
| 2014/0328842 A1 | 11/2014 | Ramakrishnan ........... | 424/133.1 |
| 2015/0239974 A1 | 8/2015 | Chang et al. ...... | C07K 16/2851 |
| 2019/0241656 A1 | 8/2019 | Endell et al. | |
| 2021/0130461 A1 | 5/2021 | Endell et al. | |
| 2022/0047632 A1 | 2/2022 | Her et al. | |
| 2022/0242952 A1 | 8/2022 | Kuffer et al. | |
| 2023/0014026 A1 | 1/2023 | Endell et al. | |
| 2024/0009196 A1 | 1/2024 | Endell et al. | |
| 2024/0156863 A1 | 5/2024 | Endell et al. | |
| 2024/0366756 A1 | 11/2024 | Amersdorffer et al. | |
| 2024/0424012 A1 | 12/2024 | Amersdorffer et al. | |

FOREIGN PATENT DOCUMENTS

| | | |
|---|---|---|
| CN | 103703027 A | 4/2014 |
| JP | 2002522511 | 7/2002 |
| JP | 2013543869 | 12/2013 |
| JP | 2014525926 | 10/2014 |
| KR | 20140071368 | 6/2014 |
| WO | WO 2002068414 | 9/2002 |
| WO | WO 2005012493 | 2/2005 |
| WO | WO 2005016326 | 2/2005 |
| WO | WO 2007002223 | 1/2007 |
| WO | WO 2007076950 | 7/2007 |

(Continued)

OTHER PUBLICATIONS

NCT01685008, Study of Fc-Optimized Anti-CD19 Antibody (MOR00208) to Treat Non-Hodgkin's Lymphoma (NHL), first posted Sep. 10, 2012.*

Kellner et al The Fc-engineered CD19 antibody MOR208 (XmAb5574) induces natural killer cell-mediated lysis of acute lymphoblastic leukemia cells from pediatric and adult patients, Leukemia, 2013, 27:1595-1598.*

Kim et al. "Influence of NK cell count on the survival of patients with diffuse large B-cell lymphoma treated with R-CHOP" Blood Research 2014 49(3):162-9.

Plonquet et al. "Peripheral blood natural killer cell count is associated with clinical outcome in patients with aaIPI 2-3 diffuse large B-cell lymphoma" Annals of Oncology 2007 18:1209-1216.

(Continued)

*Primary Examiner* — Hong Sang

(74) *Attorney, Agent, or Firm* — Fish & Richardson P.C.

(57) ABSTRACT

The present disclosure is directed to identifying characteristics and biomarkers in patients that benefit from treatment with an anti-CD19 antibody.

24 Claims, 10 Drawing Sheets

Specification includes a Sequence Listing.

(56)        References Cited

FOREIGN PATENT DOCUMENTS

| WO | WO 2008022152 | 2/2008 |
| WO | WO 2008031056 | 3/2008 |
| WO | WO 2008150494 | 12/2008 |
| WO | WO 2009052431 | 4/2009 |
| WO | WO 2010053716 | 5/2010 |
| WO | WO 2010095031 | 8/2010 |
| WO | WO 2011147834 | 12/2011 |
| WO | WO 2012010561 | 1/2012 |
| WO | WO 2012010562 | 1/2012 |
| WO | WO 2012156455 | 11/2012 |
| WO | WO 2013024095 | 2/2013 |
| WO | WO 2013024097 | 2/2013 |
| WO | WO 2013090478 | 6/2013 |
| WO | WO 2015195498 | 12/2015 |
| WO | WO 2016005548 | 1/2016 |
| WO | WO 2016189014 | 12/2016 |
| WO | WO 2017032679 | 3/2017 |
| WO | WO 2018002031 | 1/2018 |
| WO | WO 2018078123 | 5/2018 |
| WO | WO 2018220040 | 12/2018 |
| WO | WO 2020055040 | 3/2020 |
| WO | WO 2020225196 | 11/2020 |
| WO | WO 2021084062 | 5/2021 |
| WO | WO 2021084063 | 5/2021 |
| WO | WO 2021084064 | 5/2021 |
| WO | WO 2021259902 | 12/2021 |
| WO | WO 2022117799 | 6/2022 |
| WO | WO 2023118395 | 6/2023 |

OTHER PUBLICATIONS

Woyach et al. "A phase 1 trial of the Fc-engineered CD19 antibody XmAb5574 (MOR00208) demonstrates safety and preliminary effect in relapsed CLL" Blood 2014 124(24):3553-3560.

Extended European Search Report in Application No. 16171885.3 dated Nov. 9, 2016.

International Search Report and Written Opinion in PCT/EP2017/063045 dated Jul. 24, 2017.

International Preliminary Examination report in PCT/EP2017/063045 dated Dec. 4, 2018.

Office Communication dated Oct. 6, 2020 in U.S. Appl. No. 16/305,482, filed Nov. 29, 2018.

Office Communication dated Apr. 1, 2021 in U.S. Appl. No. 16/305,482, filed Nov. 29, 2018.

Office Communication dated Oct. 4, 2021 in U.S. Appl. No. 16/305,482, filed Nov. 29, 2018.

Office Communication dated Feb. 28, 2022 in U.S. Appl. No. 16/305,482, filed Nov. 29, 2018.

Awan et al. "CD19 targeting of chronic lymphocytic leukemia with a novel Fc-domain-engineered monoclonal antibody" Blood 2010 115(6):1204-1213 pp. 1-23.

Hatjiharissi et al. "Increased natural killer cell expression of CD16, augmented binding and ADCC activity to rituximab among individuals expressing the FcγRIIIa-158 V/V and V/F polymorphism" Blood 2007 110:2561-2564.

Horton et al. "Potent in vitro and in vivo Activity of an Fc-Engineered Anti-CD19 Monoclonal Antibody against Lymphoma and Leukemia" Cancer Res 2008 68(19):8049-57.

Jurczak et al. "Phase IIa study of single-agent MOR208 in patients with relapsed or refractory B-cell non-Hodgkin's lymphoma (NHL)" Journal of Clinical Oncology 2015 33(15) pp. 1-5.

Weiner, G. "Rituximab: Mechanism of Action" Seminars in Hematology 2010 47(2) :115-123.

NTC01685008 Study of Fc-Optimized Anti-CN19 Antibody to Treat Non-Hodgkin's Lymphoma (NHL) , first posted Sep. 10, 2012.

NTC01685008 Study of Fc-Optimized Anti-CN19 Antibody to Treat Non-Hodgkin's Lymphoma (NHL) , Morphosys A.G. (Year: 2015).

Bhat et al., "Serial killing of tumor cells by human natural killer cells—enhancement by therapeutic antibodies," PLoS One., Mar. 28, 2007, 2(3):e326.

Bird et al., "Single-chain antigen-binding proteins," Science, 1988, 242:423-426.

Boltezar et al., "Comparison of the algorithms classifying the ABC and GCB subtypes in diffuse large B-cell lymphoma," Oncol Lett., Mar. 12, 2018, 15:6903-6912.

Campo et al., "The 2008 WHO classification of lymphoid neoplasms and beyond: evolving concepts and practical applications," Blood, 2011, 117(19):5019-5032.

Dores et al., "Chronic lymphocytic leukaemia and small lymphocytic lymphoma: overview of the descriptive epidemiology," BJHaem., 2007, 139(5):809-819.

Extended European Search Report in Application No. 19172495.4 dated Dec. 6, 2019.

Extended European Search Report in Application No. 21170716.1, dated Nov. 10, 2021, 8 pages.

Ginaldi et al., "Levels of expression of CD19 and CD20 in chronic B cell leukaemias," J Clin Pathol., 1998, 51(5):364-369.

Hallek et al., "Guidelines for the diagnosis and treatment of chronic lymphocytic leukemia: a report from the International Workshop on Chronic Lymphocytic Leukemia updating the National Cancer Institute-Working Group 1996 guidelines," Blood, 2008, 111(12):5446-5456.

He et al., "Low natural killer (NK) cell counts in peripheral blood adversely affect clinical outcome of patients with follicular lymphoma," Blood Cancer J., Aug. 2016, 6:e457.

Hollinger et al., "Engineered antibody fragments and the rise of single domains," Nature Biotechnology, 2005, 23:1126-1136.

Huston et al., "Protein engineering of antibody binding sites: recovery of specific activity in an anti-digoxin single-chain Fv analogue produced in Escherichia coli," Proc Natl Acad Sci., 1988, 85:5879-5883.

Imgt.org [online], "Protein display: HumanIGH C-REGIONs," Mar. 23, 2001, last updated Jun. 16, 2020, retrieved from URL<http://www.imgt.org/IMGTrepertoire/Proteins/protein/human/IGH/IGHC/Hu_IGHCallgenes.html>, 1 page.

International Preliminary Report on Patentability in PCT/EP2020/062289 dated Nov. 2, 2021.

International Search Report and Written Opinion in PCT/EP2020/062289 dated Jun. 29, 2020.

Jurczak et al., "Phase IIa study of the CD19 antibody MOR208 in patients with relapsed or refractory B-cell non-Hodgkin's lymphoma," Annals of Oncology, 2018, 29:1266-1272.

Klanova et al., "Low peripheral blood NK cell count is associated with worse clinical outcome in patients with Follicular Lymphoma (FL) and Diffuse Large B-Cell Lymphoma {DLBCL) treated with immunotherapy: results from the frontline phase 3 GALLIUM and GOYA trials," Blood, 2017, 130(Suppl 1):727.

Lopez-Raton et al., "Optimal Cutpoints: An R Package for Selecting Optimal Cutpoints in Diagnostic Tests," Journal of Statistical Software, 2014, 61(8):1-36.

Olejniczak et al., "A Quantitative Exploration of Surface Antigen Expression in Common B-Cell Malignancies Using Flow Cytometry," A Journal of Molecular and Cellular Immunology, 2006, 35:93-114.

Scheuermann et al., "CD19 Antigen in Leukemia and Lymphoma Diagnosis and Immunotherapy," Leukemia and Lymphoma, 1995, 18:385-397.

Swets, "The Relative Operating Characteristic in Psychology: A technique for isolating effects of response bias finds wide use in the study of perception and cognition," Science, 1973, 182: 990-1000.

Ward et al., "Binding activities of a repertoire of single immunoglobulin variable domains secreted from Escherichia coli," Nature, 1989, 341:544-546.

Zapata et al., "Engineering linear F(ab')2 fragments for efficient production in Escherichia coli and enhanced antiproliferative activity," Protein Eng., 1995, 8(10):1057-1062.

Makita et al., "Antibody therapy targeting CD19 for B-cell non-Hodgkin's lymphoma," Annals of Oncology, Mar. 2018, 29(25):1086-1089.

(56) References Cited

OTHER PUBLICATIONS

Romain et al., "Antibody FC engineering improves frequency and promotes kinetic boosting of serial killing mediated by NK cells," Blood, 2014, 124(22):3241-3249.

* cited by examiner

FIG. 1

The amino acid sequence of the MOR00208 Variable Heavy Domain is (The CDRs are bolded and underlined):

> EVQLVESGGGLVKPGGSLKLSCAASGYTFTSYVMHWVRQAPGKGLEWIGYI
> NPYNDGTKYNEKFQGRVTISSDKSISTAYMELSSLRSEDTAMYYCARGTYYY
> GTRVFDYWG QGTLVTVSS (SEQ ID NO: 10)

The amino acid sequence of the MOR00208 Variable Light Domain is (The CDRs are bolded and underlined):

> DIVMTQSPATLSLSPGERATLSCRSSKSLQNVNGNTYLYWFQQKPGQSPQL
> LIYRMSNLNSGVPDRFSGSGSGTEFTLTISSLEPEDFAVYYCMQHLEYPITFG
> AGTKLEIK (SEQ ID NO: 11)

The amino acid sequence of the MOR00208 HCDR1 is: SYVMH (SEQ ID NO: 1)

The amino acid sequence of the MOR00208 HCDR2 is: NPYNDG (SEQ ID NO: 2)

The amino acid sequence of the MOR00208 HCDR3 is: GTYYYGTRVFDY (SEQ ID NO: 3)

The amino acid sequence of the MOR00208 LCDR1 is: RSSKSLQNVNGNTYLY (SEQ ID NO: 4)

The amino acid sequence of the MOR00208 LCDR2 is: RMSNLNS (SEQ ID NO: 5)

The amino acid sequence of the MOR00208 LCDR3 is: MQHLEYPIT (SEQ ID NO: 6)

FIG. 2

The amino acid sequence of the MOR00208 Heavy Chain is:

EVQLVESGGGLVKPGGSLKLSCAASGYTFTSYVMHWVRQAPGKGLEWIGYINPYNDGTKY

NEKFQGRVTISSDKSISTAYMELSSLRSEDTAMYYCARGTYYYGTRVFDYWGQGTLVTVSS

ASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKKVEPKSCDKTHTCPPCPAPELLGGPDV

FLFPPKPKDTLMISRTPEVTCVVVDVSHEDPEVQFNWYVDGVEVHNAKTKPREEQFNSTFR

VVSVLTVVHQDWLNGKEYKCKVSNKALPAPEEKTISKTKGQPREPQVYTLPPSREEMTKNQ

VSLTCLVKGFYPSDIAVEWESNGQPENNYKTTPPMLDSDGSFFLYSKLTVDKSRWQQGNV

FSCSVMHEALHNHYTQKSLSLSPGK (SEQ ID NO: 8)

The amino acid sequence of the MOR00208 Light Chain is:

DIVMTQSPATLSLSPGERATLSCRSSKSLQNVNGNTYLYWFQQKPGQSPQLLIYRMSNLN

SGVPDRFSGSGSGTEFTLTISSLEPEDFAVYYCMQHLEYPITFGAGTKLEIKRTVAAPSVFIFP

PSDEQLKSGTASVVCLLNNFYPREAKVQWKVDNALQSGNSQESVTEQDSKDSTYSLSSTLT

LSK ADYEKHKVYACEVTHQGLSSPVTKSFNRGEC (SEQ ID NO: 9)

FIG. 3

Determining the cut offs for peripheral NK cell counts via ROC analysis

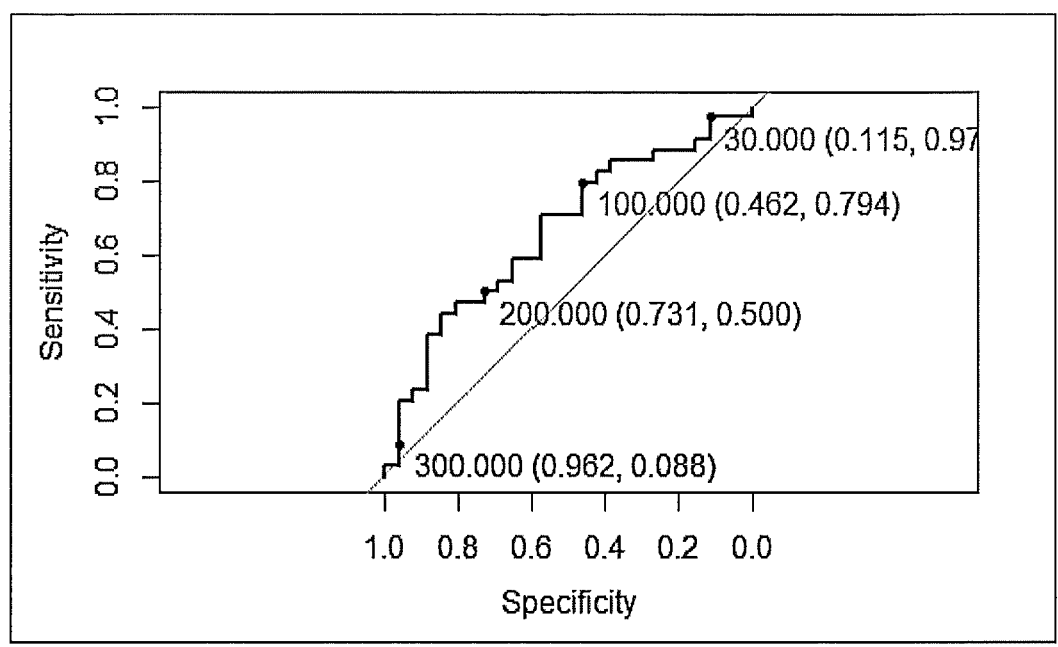

Receiver Operating Characteristic (ROC) analysis of peripheral NK cell count (cells/µl) as a predictor for the Disease Control Rate (CR, PR, DS vs PD, ET) in DLBCL and iNHL patients. Various cut offs with Specificity and Sensitivity values are displayed. AUC = 0.66. CR-Complete Remission, PR-Partial Remission, SD-Stable Disease, PD-Progressive Disease, ET-Early Termination, ABC-Antigens Bound per Cell.

FIG. 4

Determining the cut offs for CD16 expression (ABC) via ROC analysis

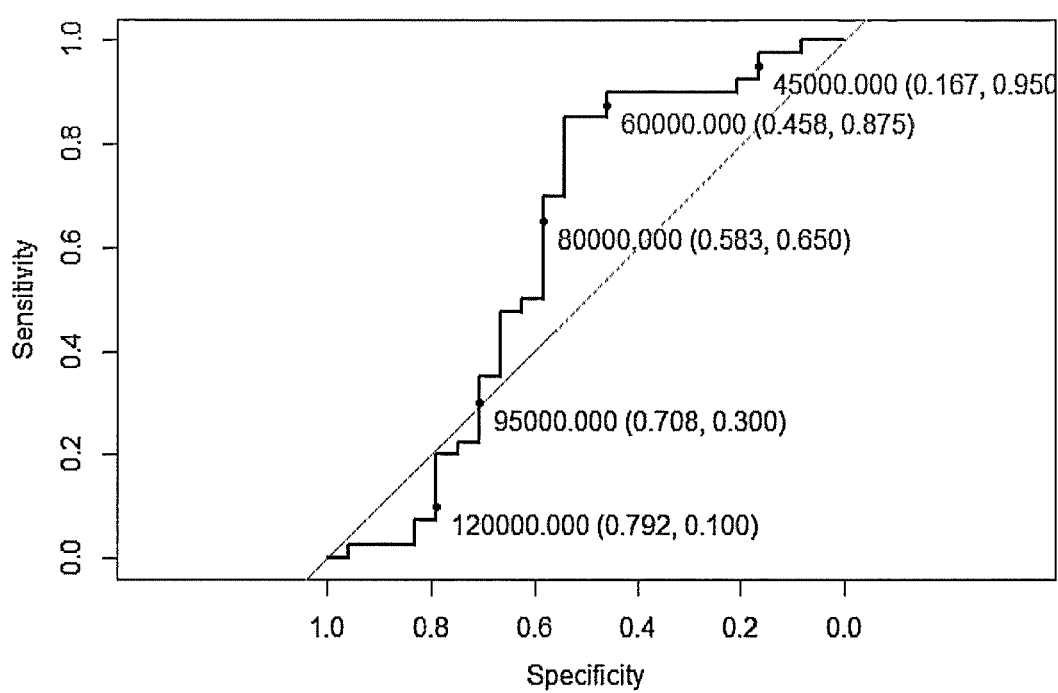

Receiver Operating Characteristic (ROC) analysis of CD16 expression (ABC) as a predictor for the Disease Control Rate (CR, PR, DS vs PD, ET) in DLBCL and iNHL patients. Various cut offs with Specifity and Sensitivity values are displayed. AUC = 0.61. CR-Complete Remission, PR-Partial Remission, SD-Stable Disease, PD-Progressive Disease, ET-Early Termination, ABC-Antigens Bound per Cell.

FIG. 5

Determining the cut offs for peripheral T cell count via ROC analysis

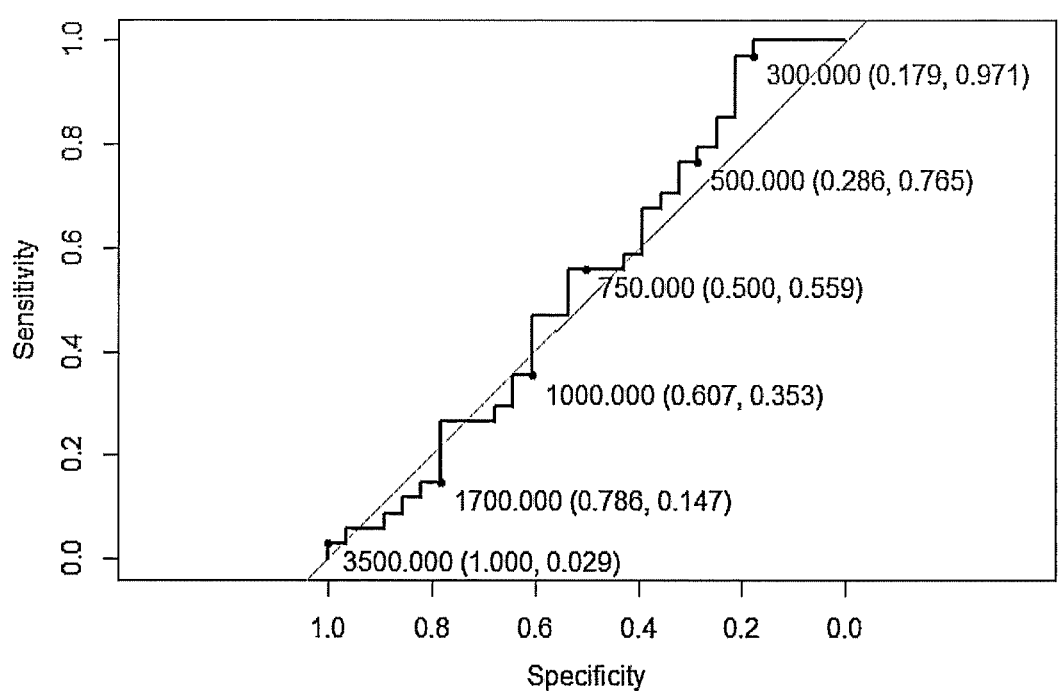

Receiver Operating Characteristic (ROC) analysis of peripheral T cell count (cells/µl) as a potential predictor for the Disease Control Rate (CR, PR, DS vs PD, ET) in DLBCL and iNHL patients. Various cut offs with Specifity and Sensitivity values are displayed. AUC = 0.53. CR-Complete Remission, PR-Partial Remission, SD-Stable Disease, PD-Progressive Disease, ET-Early Termination, ABC-Antigens Bound per Cell.

ABC-Antigens Bound per Cell. Analysis of correlation: Pearson r = 0,019 with two-tailed p value = 0.9; Nonparametric Spearman r = 0,036 with two-tailed p value = 0.8; n = 51.

Figure 7:
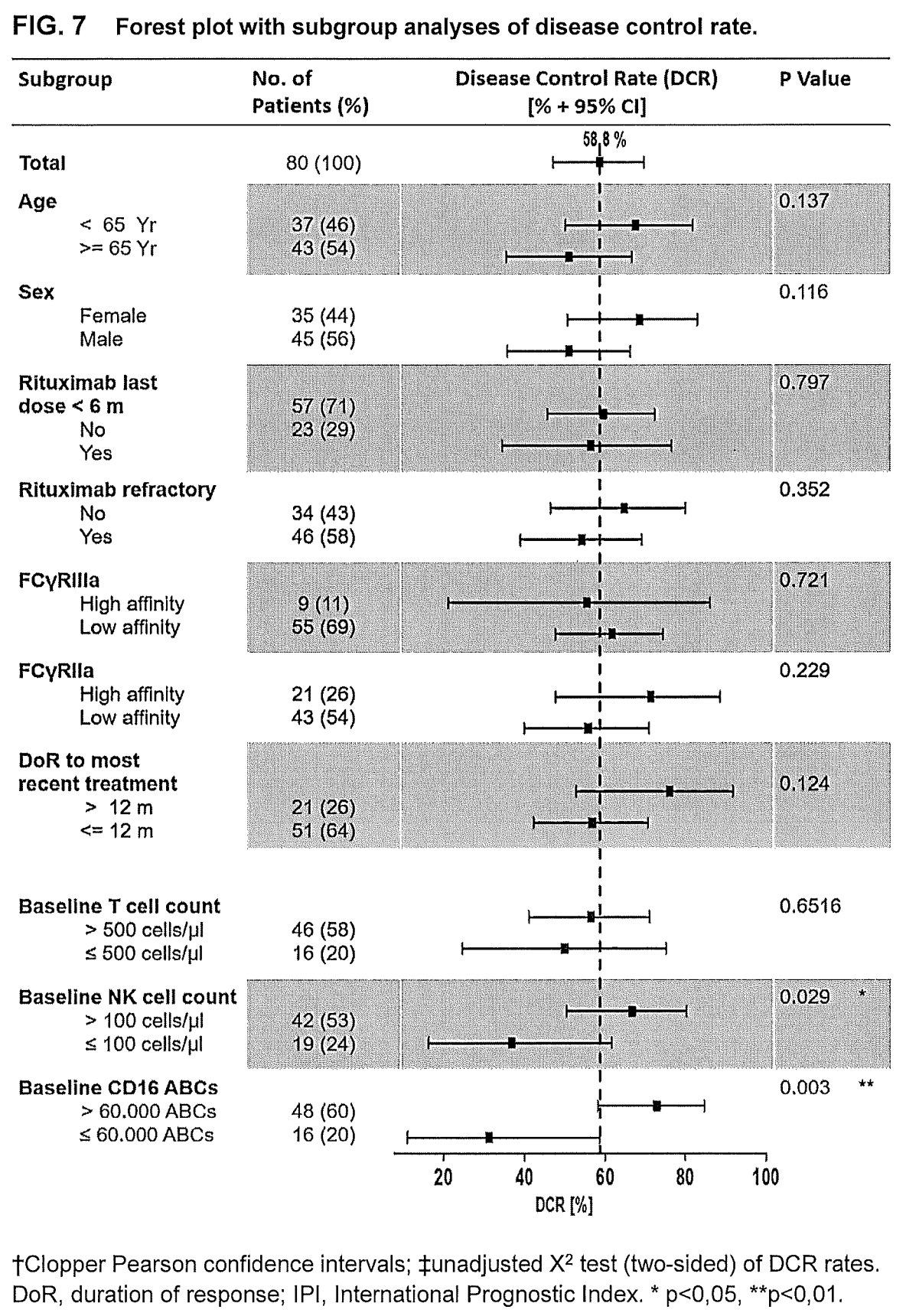

FIG. 7    Forest plot with subgroup analyses of disease control rate.

| Subgroup | No. of Patients (%) | Disease Control Rate (DCR) [% + 95% CI] | P Value |
|---|---|---|---|
| Total | 80 (100) | 58,8 % | |
| Age | | | 0.137 |
| < 65 Yr | 37 (46) | | |
| >= 65 Yr | 43 (54) | | |
| Sex | | | 0.116 |
| Female | 35 (44) | | |
| Male | 45 (56) | | |
| Rituximab last dose < 6 m | | | 0.797 |
| No | 57 (71) | | |
| Yes | 23 (29) | | |
| Rituximab refractory | | | 0.352 |
| No | 34 (43) | | |
| Yes | 46 (58) | | |
| FCγRIIIa | | | 0.721 |
| High affinity | 9 (11) | | |
| Low affinity | 55 (69) | | |
| FCγRIIa | | | 0.229 |
| High affinity | 21 (26) | | |
| Low affinity | 43 (54) | | |
| DoR to most recent treatment | | | 0.124 |
| > 12 m | 21 (26) | | |
| <= 12 m | 51 (64) | | |
| Baseline T cell count | | | 0.6516 |
| > 500 cells/μl | 46 (58) | | |
| ≤ 500 cells/μl | 16 (20) | | |
| Baseline NK cell count | | | 0.029 * |
| > 100 cells/μl | 42 (53) | | |
| ≤ 100 cells/μl | 19 (24) | | |
| Baseline CD16 ABCs | | | 0.003 ** |
| > 60.000 ABCs | 48 (60) | | |
| ≤ 60.000 ABCs | 16 (20) | | |

DCR [%] (axis: 20  40  60  80  100)

†Clopper Pearson confidence intervals; ‡unadjusted $X^2$ test (two-sided) of DCR rates. DoR, duration of response; IPI, International Prognostic Index. * $p<0,05$, ** $p<0,01$.

FIG. 8 Subgroup analysis of Progression-free survival (PFS)
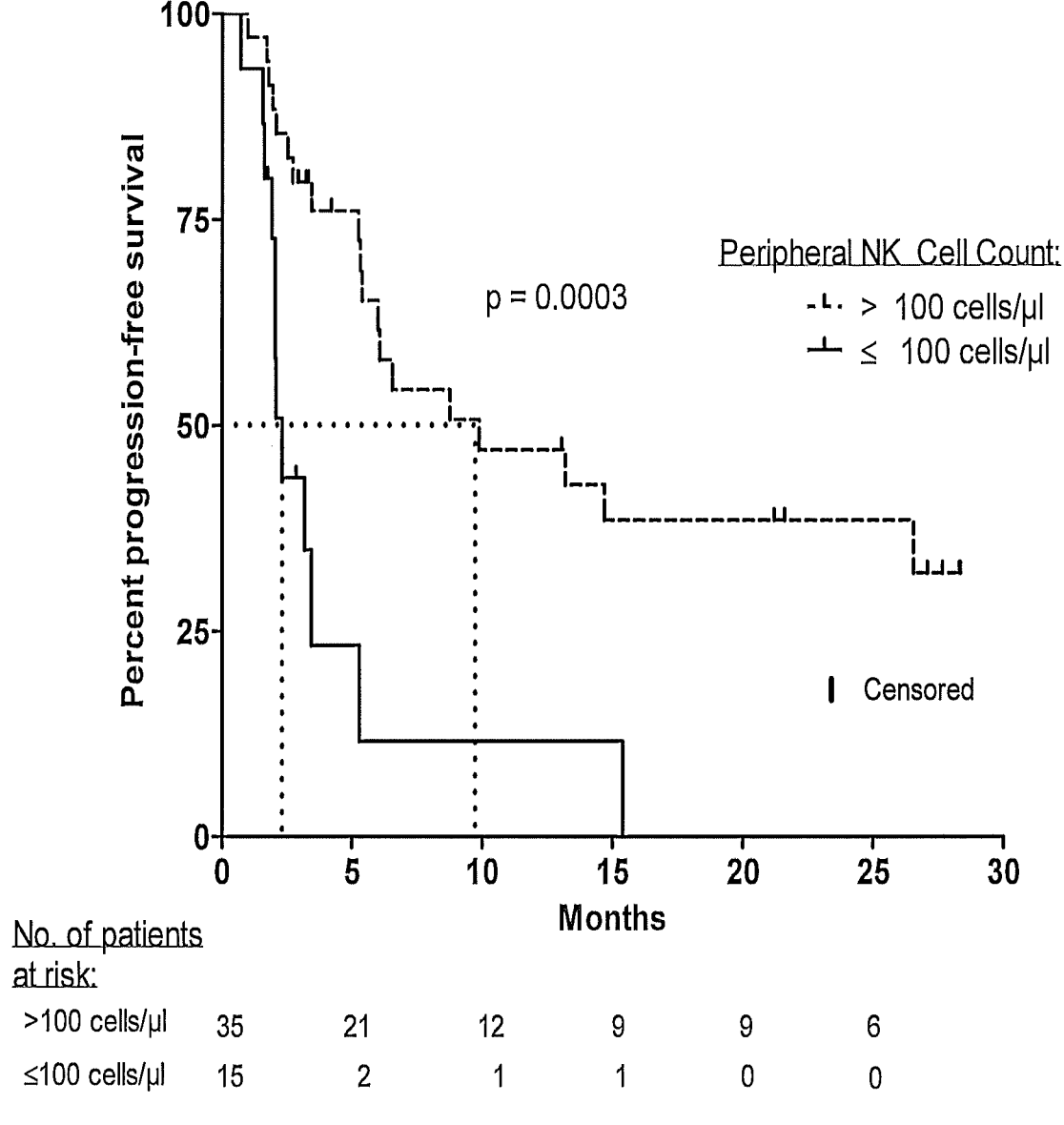
Patients without post baseline radiological tumor assessment were censored at baseline. PFS, progression-free survival. Unadjusted log-rank p value = 0.0003.

FIG. 9 Subgroup analysis of Progression-free survival (PFS)
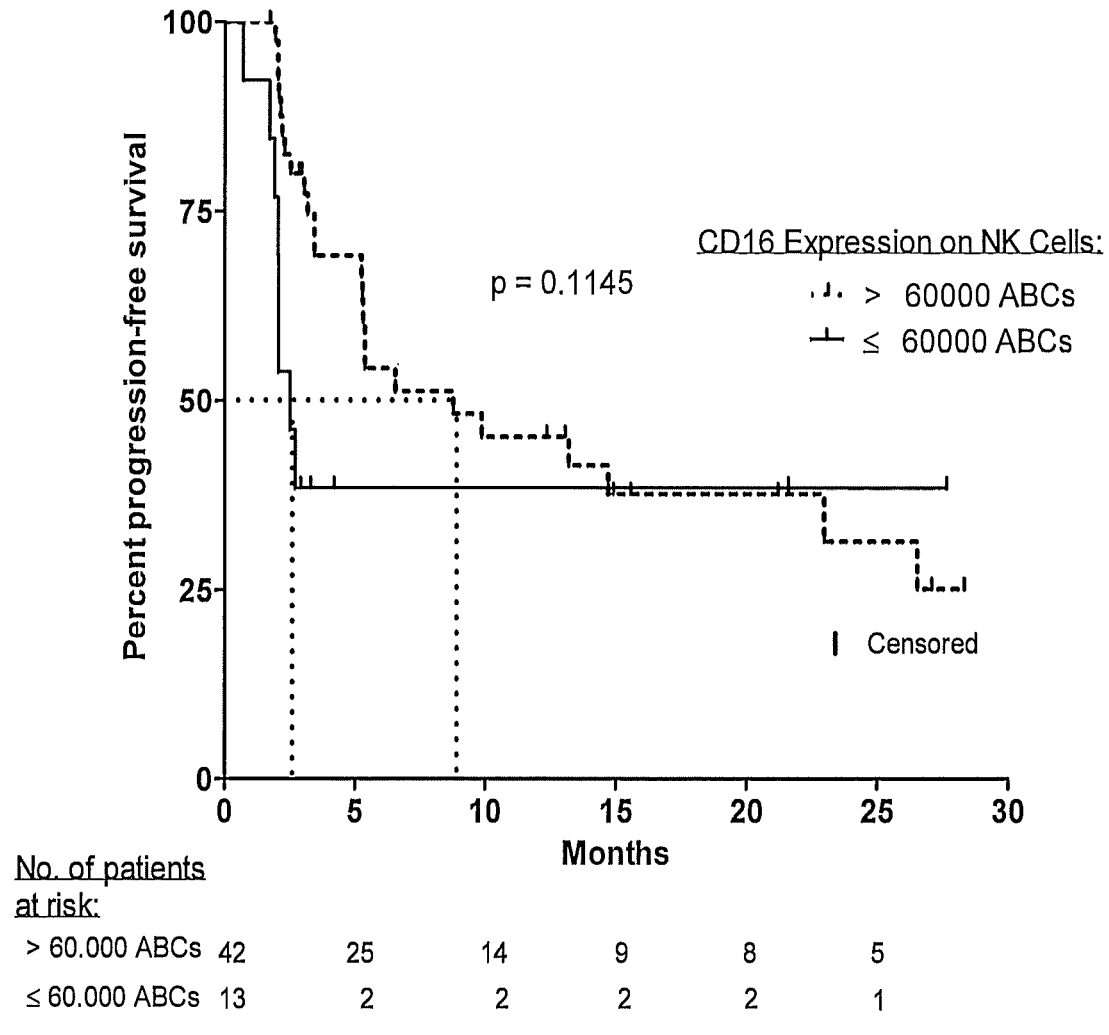
Patients without post baseline radiological tumor assessment were censored at baseline. PFS, progression-free survival. Unadjusted log-rank p value = 0.1145

FIG. 10 Subgroup analysis of Progression-free survival (PFS)
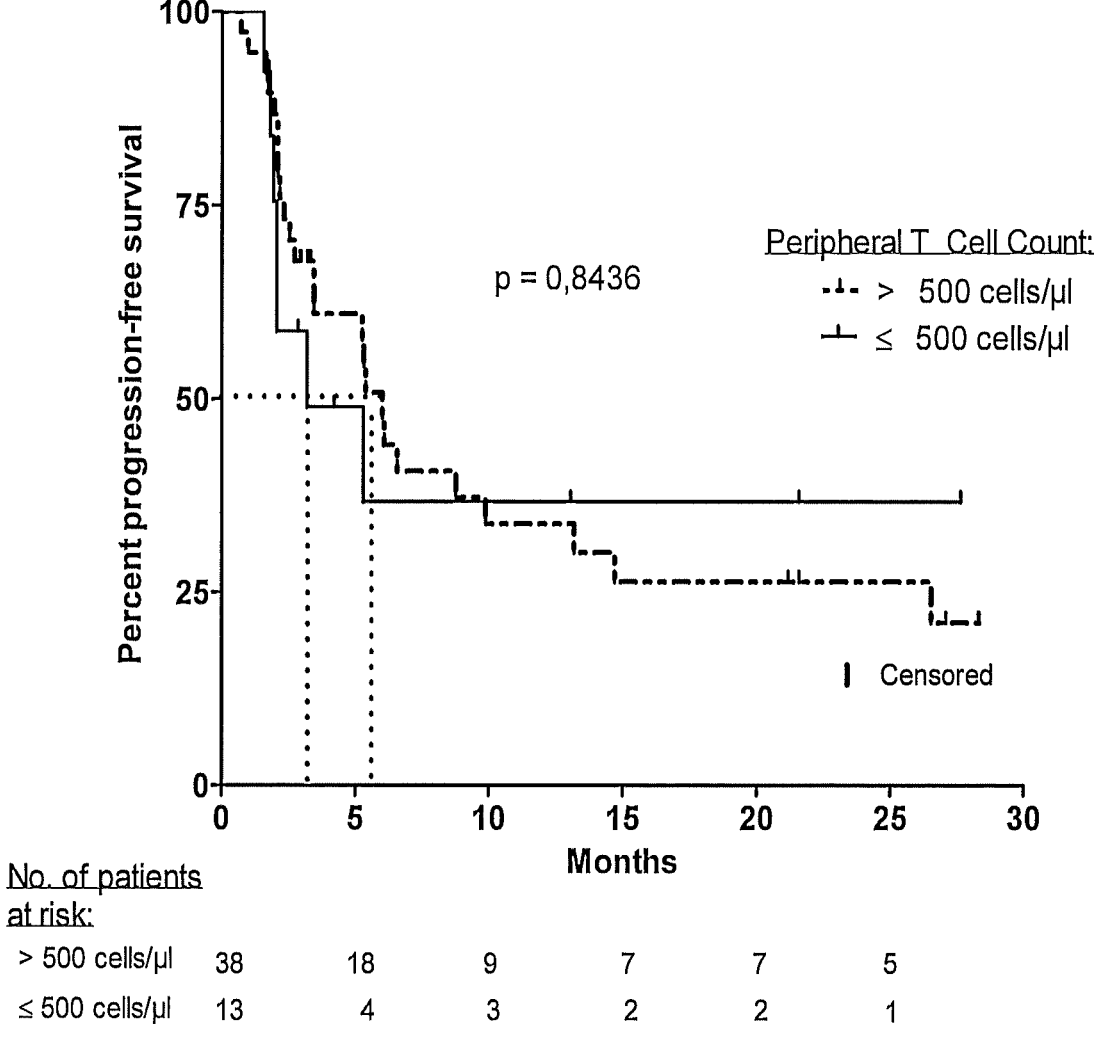
No. of patients
at risk:
| | | | | | | |
|---|---|---|---|---|---|---|
| > 500 cells/µl | 38 | 18 | 9 | 7 | 7 | 5 |
| ≤ 500 cells/µl | 13 | 4 | 3 | 2 | 2 | 1 |
Patients without post baseline radiological tumor assessment were censored at baseline. PFS, progression-free survival. Unadjusted log-rank p value = 0.8436

SEQUENCE LISTING

```
<160> NUMBER OF SEQ ID NOS: 13

<210> SEQ ID NO 1
<211> LENGTH: 5
<212> TYPE: PRT
<213> ORGANISM: Artificial sequence
<220> FEATURE:
<223> OTHER INFORMATION: synthetic construct

<400> SEQUENCE: 1

Ser Tyr Val Met His
1               5

<210> SEQ ID NO 2
<211> LENGTH: 6
<212> TYPE: PRT
<213> ORGANISM: Artificial sequence
<220> FEATURE:
<223> OTHER INFORMATION: synthetic construct

<400> SEQUENCE: 2

Asn Pro Tyr Asn Asp Gly
1               5

<210> SEQ ID NO 3
<211> LENGTH: 12
<212> TYPE: PRT
<213> ORGANISM: Artificial sequence
<220> FEATURE:
<223> OTHER INFORMATION: synthetic construct

<400> SEQUENCE: 3

Gly Thr Tyr Tyr Tyr Gly Thr Arg Val Phe Asp Tyr
1               5                   10
```

<210> SEQ ID NO 4
<211> LENGTH: 16
<212> TYPE: PRT
<213> ORGANISM: Artificial sequence
<220> FEATURE:
<223> OTHER INFORMATION: synthetic construct

<400> SEQUENCE: 4

Arg Ser Ser Lys Ser Leu Gln Asn Val Asn Gly Asn Thr Tyr Leu Tyr
1               5                   10                  15

<210> SEQ ID NO 5
<211> LENGTH: 7
<212> TYPE: PRT
<213> ORGANISM: Artificial sequence
<220> FEATURE:
<223> OTHER INFORMATION: synthetic construct

<400> SEQUENCE: 5

Arg Met Ser Asn Leu Asn Ser
1               5

<210> SEQ ID NO 6
<211> LENGTH: 9
<212> TYPE: PRT
<213> ORGANISM: Artificial sequence
<220> FEATURE:
<223> OTHER INFORMATION: synthetic construct

<400> SEQUENCE: 6

Met Gln His Leu Glu Tyr Pro Ile Thr
1               5

<210> SEQ ID NO 7
<211> LENGTH: 556
<212> TYPE: PRT
<213> ORGANISM: Homo sapiens
<220> FEATURE:
<223> OTHER INFORMATION: CD19

<400> SEQUENCE: 7

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
            165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
            195                 200                 205

Arg Gly Pro Leu Ser Trp Thr His Val His Pro Lys Gly Pro Lys Ser
        210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
        290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
                340                 345                 350

Ser Leu Pro Thr Pro Thr Ser Gly Leu Gly Arg Ala Gln Arg Trp Ala
            355                 360                 365

Ala Gly Leu Gly Gly Thr Ala Pro Ser Tyr Gly Asn Pro Ser Ser Asp
        370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
            435                 440                 445

Pro Glu Asp Glu Asp Ser Phe Ser Asn Ala Glu Ser Tyr Glu Asn Glu
        450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
            515                 520                 525

Asp Ser Tyr Glu Asn Met Asp Asn Pro Asp Gly Pro Asp Pro Ala Trp
        530                 535                 540

Gly Gly Gly Gly Arg Met Gly Thr Trp Ser Thr Arg
545                 550                 555

<210> SEQ ID NO 8
<211> LENGTH: 451
<212> TYPE: PRT

```
<213> ORGANISM: Artificial sequence
<220> FEATURE:
<223> OTHER INFORMATION: synthetic construct

<400> SEQUENCE: 8

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Asp Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
            275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Ala Leu Pro Ala Pro Glu
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
```

```
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 9
<211> LENGTH: 219
<212> TYPE: PRT
<213> ORGANISM: Artificial sequence
<220> FEATURE:
<223> OTHER INFORMATION: synthetic construct

<400> SEQUENCE: 9

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
                20                  25                  30

Asn Gly Asn Thr Tyr Leu Tyr Trp Phe Gln Gln Lys Pro Gly Gln Ser
            35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 10
<211> LENGTH: 121
<212> TYPE: PRT
<213> ORGANISM: Artificial sequence
<220> FEATURE:
<223> OTHER INFORMATION: synthetic construct

<400> SEQUENCE: 10

Glu Val Gln Leu Val Glu Ser Gly Gly Gly Leu Val Lys Pro Gly Gly
1               5                   10                  15
```

-continued

```
Ser Leu Lys Leu Ser Cys Ala Ala Ser Gly Tyr Thr Phe Thr Ser Tyr
        20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
        50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
                100                 105                 110

Gln Gly Thr Leu Val Thr Val Ser Ser
        115                 120
```

<210> SEQ ID NO 11
<211> LENGTH: 112
<212> TYPE: PRT
<213> ORGANISM: Artificial sequence
<220> FEATURE:
<223> OTHER INFORMATION: synthetic construct

<400> SEQUENCE: 11

```
Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
        20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
        50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
                100                 105                 110
```

<210> SEQ ID NO 12
<211> LENGTH: 330
<212> TYPE: PRT
<213> ORGANISM: Artificial sequence
<220> FEATURE:
<223> OTHER INFORMATION: synthetic construct

<400> SEQUENCE: 12

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
        20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Val
            180                 185                 190

His Gln Asp Trp Leu Asn Gly Lys Glu Tyr Lys Cys Lys Val Ser Asn
            195                 200                 205

Lys Ala Leu Pro Ala Pro Glu Glu Lys Thr Ile Ser Lys Thr Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Met Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330
```

<210> SEQ ID NO 13
<211> LENGTH: 107
<212> TYPE: PRT
<213> ORGANISM: Artificial sequence
<220> FEATURE:
<223> OTHER INFORMATION: synthetic construct

<400> SEQUENCE: 13

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

METHODS FOR PREDICTING THERAPEUTIC BENEFIT OF ANTI-CD19 THERAPY IN PATIENTS

This patent application is a continuation of U.S. application Ser. No. 16/305,482 filed Nov. 29, 2018, which is the National Stage of International Application No. PCT/EP2017/063045 filed May 30, 2017, which claims the benefit of priority from EP 16171885.3 filed May 30, 2016, each of which is incorporated by reference in its entirety.

FIELD OF THE INVENTION

The present disclosure is directed to identifying characteristics and biomarkers in patients that benefit from treatment with anti-CD19 antibodies.

BACKGROUND

CD19 is a 95-kDa transmembrane glycoprotein of the immunoglobulin superfamily containing two extracellular immunoglobulin-like domains and an extensive cytoplasmic tail. The protein is a pan-B lymphocyte surface receptor and is ubiquitously expressed from the earliest stages of pre-B cell development onwards until it is down-regulated during terminal differentiation into plasma cells. It is B-lymphocyte lineage specific and not expressed on hematopoietic stem cells and other immune cells, except some follicular dendritic cells. CD19 functions as a positive regulator of B cell receptor (BCR) signaling and is important for B cell activation and proliferation and in the development of humoral immune responses. It acts as a co-stimulatory molecule in conjunction with CD21 and CD81 and is critical for B cell responses to T-cell-dependent antigens. The cytoplasmic tail of CD19 is physically associated with a family of tyrosine kinases that trigger downstream signaling pathways via the src-family of protein tyrosine kinases. CD19 is an attractive target for cancers of lymphoid origin since it is highly expressed in nearly all chronic lymphocytic leukemia (CLL) and non-Hodgkin's lymphomas (NHL), as well as many other different types of leukemias, including acute lymphocytic leukemia (ALL) and hairy cell leukemia (HCL).

The clinical development of CD19 directed antibodies had previously been limited by the internalization of the CD19 antigen, however, improved antibody modification technology has restored this potential therapeutic target. MOR00208 (previously named XmAb5574) is an Fc engineered humanized monoclonal antibody that binds CD19. The increase in binding of MOR00208 Fc to FcγR, due to XmAb engineered mutations, significantly enhances in-vitro antibody dependent cell-mediated cytotoxicity (ADCC), antibody dependent cell-mediated phagocytosis (ADCP), and direct cytotoxic effects (apoptosis) on tumor relative to the unmodified antibody. MOR00208 has not been shown to mediate complement dependent cytotoxicity.

MOR00208 has or is currently being studied in clinical trials in CLL, ALL and NHL. Specifically, a Phase I trial titled Safety and Tolerability of XmAb®5574 in Chronic Lymphocytic Leukemia, and a Phase IIa trial titled Study of Fc-Optimized Anti-CD19 Antibody (MOR00208) to treat B-cell Acute Lymphoblastic Leukemia (B-ALL) are completed. A Phase IIa trial titled Study of Fc-Optimized Anti-CD19 Antibody (MOR00208) to Treat Non-Hodgkin's Lymphoma (NHL) has completed recruitment. And the following trials are planned/ongoing: a Phase II/III trial titled A Trial to Evaluate the Efficacy and Safety of MOR00208 With Bendamustine (BEN) Versus Rituximab (RTX) With BEN in Adult Patients With Relapsed or Refractory Diffuse Large B-cell Lymphoma (DLBCL) (B-MIND), a Phase II trial titled Study to Evaluate Efficacy and Safety of MOR00208 With Idelalisib in R/R CLL/SLL Patients Pretreated With BTKi, a Phase II trial titled A Study to Evaluate the Safety and Efficacy of Lenalidomide With MOR00208 in Patients With R-R DLBCL, and a Phase II trial titled Phase II MOR00208 in Combination With Lenalidomide for Patients With Relapsed or Refractory CLL, SLL or PLL or Older Patients With Untreated CLL, SLL or PLL. In a further current Phase II trial (COSMOS) the Efficacy and Safety of MOR00208 in combination with idelalisib or venetoclax in Patients with Relapsed or Refractory CLL, SLL is studied.

Single agent efficacy of MOR00208 has been reported in CLL, and NHL. The general variable response rates of patients to monoclonal antibody therapies, however, indicate that methods are needed to accurately predict which patients are likely to respond to such antibody therapies so that the treatment can be administered to those patients who are most likely to receive benefits. Particular biomarkers or characteristics of patients may be found for which a particular concentration or range for each biomarker correlates with responsiveness to such therapy.

The influence of natural killer (NK) cell count on the survival of patients with DLBCL treated with Rituximab, Cyclophosphamide, Doxorubicin Hydrochloride (Hydroxydaunomycin), Vincristine Sulfate (Oncovin) and Prednisone (R-CHOP) was evaluated. Kim et al., Blood Research, 49:3, 162-169 (September 2014). Previously, it was reported that peripheral NK cell count was associated with clinical outcome in patients with aaIPI 2-3 DLBCL. Plonquet et al., Ann Oncol 2007; 18:1209-15.

It is clear that significant efforts and investment are needed to discover and identify such patient characteristics and biomarkers predictive of efficacy.

SUMMARY OF INVENTION

MOR00208 has been studied in patients having CLL, ALL, NHL and SLL. Accordingly, a thorough analysis of clinical data has been completed to date in order to identify characteristics or biomarkers of patients that are more likely to benefit from MOR00208 treatment.

MOR00208 specifically targets the CD19 surface antigen and mediates direct tumor cell killing via its enhanced ADCC effector function. In preclinical studies, MOR00208 has been shown to significantly enhance in vitro ADCC, ADCP, and direct cytotoxic effects (apoptosis) on CD19$^+$ tumor cell lines spanning a broad range of human lymphomas and leukemias (Burkitt's lymphoma, CLL, hairy cell leukemia (HCL), CD19+ chronic myeloid leukemia (CML), diffuse large B cell lymphoma (DLBCL) and acute lymphoblastic leukemia (ALL), expressing levels of CD19 antigen ranging from 15,000 to 105,000 molecules/cell. Similar effects have also been observed in relation to freshly isolated patient CLL or ALL cells and are also expected to translate to primary non-Hodgkin's lymphoma (NHL) cells since the expression range reported for ALL and CLL B cells covers the range observed for NHL B cells (Ginaldi et al., 1998; Olejniczak et al., 2006). Based on the widely and homogenous surface expression of CD19 throughout various types of B cell neoplasms the effect of MOR00208 in the present study can be transferred to a broad range of human lymphomas and leukemias, such as CLL, ALL, NHL and SLL and subtypes thereof.

Data from the Phase IIa trial titled Study of Fc-Optimized Anti-CD19 Antibody (MOR00208) to Treat Non-Hodgkin's Lymphoma (NHL) has been thoroughly analyzed. As a result of these efforts, the following disclosure provides characteristics and biomarkers of patients where anti-CD19 antibodies are efficacious.

Specifically at least the following characteristics of patients were evaluated: a) age, b) gender, c) if patients had received a dose of Rituximab within the last 6 months, d) whether the patients were Rituximab refractory, e) whether patients have the FCgammaRIIIa high or low affinity allele, f) whether patients have the FCgammaRIIa high or low affinity allele, g) whether patients had a duration of response to the previous treatment of greater than 12 months, h) baseline peripheral T cell counts (cells/µl), i) baseline peripheral NK cell count (cells/µl) and j) baseline CD16 expression on peripheral NK cells (Antibodies Bound per Cells-ABCs).

Both 1) baseline peripheral NK cell counts and 2) baseline CD16 expression on peripheral NK cells showed clear correlations to patient responses with MOR00208 therapy. Specifically, patients having a higher baseline peripheral NK cell count per µl correlated with a higher Disease Control Rate (DCR). DCR includes patients have Complete Response (CR)+Partial Response (PR)+Stable Disease (SD). Additionally, such patients had a significantly better Progression Free Survival (PFS) as compared to patients having lower NK cells counts. In addition, patients having a baseline CD16 expression on NK cells of at least 60,000 (ABCs) correlated with higher Disease Control Rate (DCR).

Therefore, patients diagnosed with CLL, ALL, NHL and SLL and having either a) a high peripheral NK cell count or 2) baseline CD16 expression on peripheral NK cells of at least 60,000 ABCs are more likely to benefit from MOR00208 treatment.

Both 1) baseline peripheral NK cell counts and 2) baseline CD16 expression on peripheral NK cells showed clear correlations to patient responses with MOR00208 therapy. Specifically, patients having a baseline peripheral NK cell count of at least 50 cells/µl correlated with a higher Disease Control Rate (DCR). DCR includes patients have Complete Response (CR)+Partial Response (PR)+Stable Disease (SD). Additionally, patients having a baseline NK cell count of at least 50 cells/µl had a significantly better Progression Free Survival (PFS) as compared to patients having lower NK cells counts. In addition, patients having a baseline CD16 expression on NK cells of at least 60,000 (ABCs) correlated with higher Disease Control Rate (DCR).

Therefore, patients diagnosed with CLL, ALL, NHL and SLL and having either a) baseline peripheral NK cell count of at least 50 cells/µl or 2) baseline CD16 expression on peripheral NK cells of at least 60,000 ABCs are more likely to benefit from MOR00208 treatment.

Both 1) baseline peripheral NK cell counts and 2) baseline CD16 expression on peripheral NK cells showed clear correlations to patient responses with MOR00208 therapy. Specifically, patients having a baseline peripheral NK cell count of at least 100 cells/µl correlated with a higher Disease Control Rate (DCR). DCR includes patients have Complete Response (CR)+Partial Response (PR)+Stable Disease (SD). Additionally, patients having a baseline NK cell count of at least 100 cells/µl had a significantly better Progression Free Survival (PFS) as compared to patients having lower NK cells counts. In addition, patients having a baseline CD16 expression on NK cells of at least 60,000 (ABCs) correlated with higher Disease Control Rate (DCR).

Therefore, patients diagnosed with CLL, ALL, NHL and SLL and having either a) baseline peripheral NK cell count of at least 100 cells/µl or 2) baseline CD16 expression on peripheral NK cells of at least 60,000 ABCs are more likely to benefit from MOR00208 treatment.

DESCRIPTION OF DRAWINGS

FIG. 1 shows the amino acid sequences of MOR00208 variable domains and CDRs.

FIG. 2 shows the amino acid sequences of MOR00208's full heavy and light chains.

FIG. 3 shows the Receive Operating Characteristic (ROC) analysis of peripheral NK cell counts as a predictor for DCR.

FIG. 4 shows the ROC analysis of CD16 expression levels on peripheral NK cells (ABCs) as a predictor for DCR.

FIG. 5 shows the ROC analysis of peripheral T cell count as a potential predictor for DCR.

FIG. 7 shows the Forest Plot with DCRs in patient subgroups with specific baseline characteristics and bio-markers FIG. 8 shows the progression free survival difference between patients having at least 100 cells/µl peripheral NK cell counts versus patients having lower NK cell counts.

FIG. 9 shows the progression free survival difference between patients having at least 60,000 ABCs in CD16 expression on peripheral NK cells versus patients having lower CD16 expression on NK cells.

FIG. 10 shows the progression free survival difference between patients having at least 500 cells/µl peripheral T cell counts versus patients having lower T cell counts.

DETAILED DESCRIPTION

Figure 6:
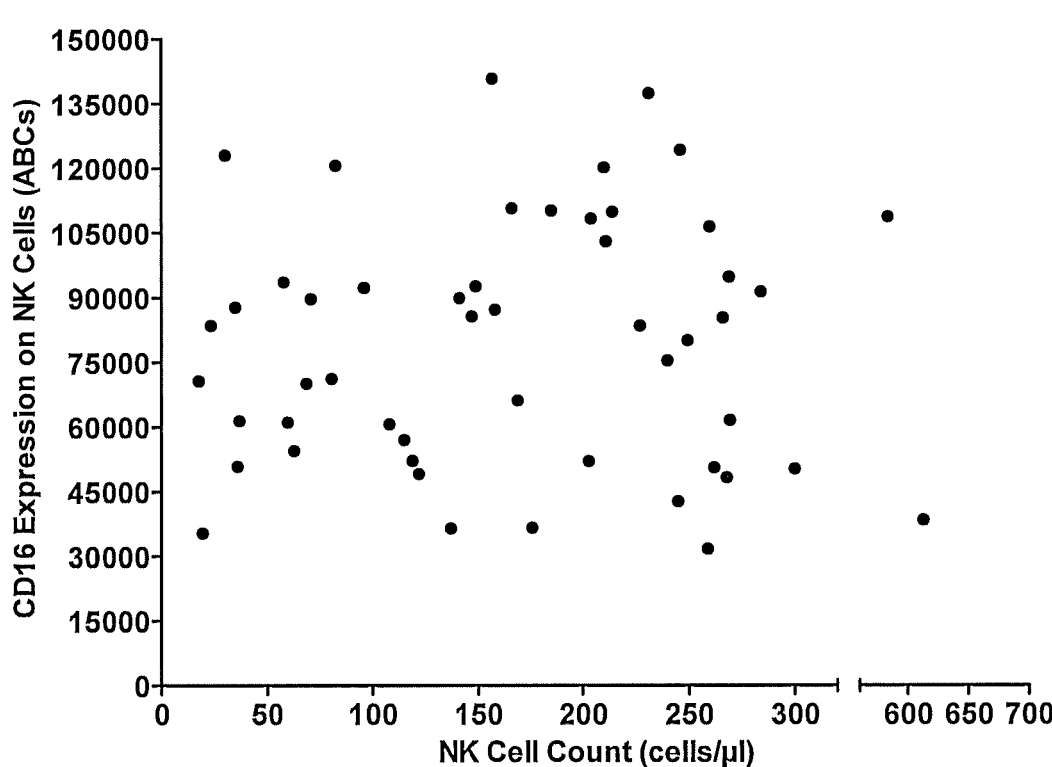
FIG. 6 shows that peripheral NK cell counts and CD16 expression levels on peripheral NK cells are independent variables and not correlated.

The term "antibody" means monoclonal antibodies, including any isotype, such as, IgG, IgM, IgA, IgD and IgE. An IgG antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are referred to as CDR1, CDR2, and CDR3, numbered sequentially from the N-terminus. The more highly conserved portions of the variable regions outside of the CDRs are called the "framework regions". An "antibody fragment" means an Fv, scFv, dsFv, Fab, Fab' F(ab')2 fragment, or other fragment, which contains at least one variable heavy or variable light chain, each containing CDRs and framework regions.

"VH" refers to the variable region of an immunoglobulin heavy chain of an antibody, or antibody fragment. "VL" refers to the variable region of the immunoglobulin light chain of an antibody, or antibody fragment.

"Fc region" means the constant region of an antibody, which in humans may be of the IgG1, 2, 3, 4 subclass or others. The sequences of human Fc regions are available at IMGT, Human IGH C-REGIONs, imgt. with the extension org/IMGTrepertoire/Proteins/protein/human/IGH/IGHC/Hu_IGHCallgenes.html of the world wide web (retrieved on 16 May 2011).

The term patient includes a human.

NHL is a heterogeneous malignancy originating from lymphocytes. In the United States (U.S.), the incidence is estimated at 65,000/year with mortality of approximately 20,000 (American Cancer Society, 2006; and SEER Cancer Statistics Review). The disease can occur in all ages, the usual onset begins in adults over 40 years, with the incidence increasing with age. NHL is characterized by a clonal proliferation of lymphocytes that accumulate in the lymph nodes, blood, bone marrow and spleen, although any major organ may be involved. The current classification system used by pathologists and clinicians is the World Health Organization (WHO) Classification of Tumours, which organizes NHL into precursor and mature B-cell or T-cell neoplasms. The PDQ is currently dividing NHL as indolent or aggressive for entry into clinical trials. The indolent NHL group is comprised primarily of follicular subtypes, small lymphocytic lymphoma, MALT (mucosa-associated lymphoid tissue), and marginal zone; indolent encompasses approximately 50% of newly diagnosed B-cell NHL patients. Aggressive NHL includes patients with histologic diagnoses of primarily diffuse large B cell (DLBL, DLBCL, or DLCL) (40% of all newly diagnosed patients have diffuse large cell), Burkitt's, and mantle cell. The clinical course of NHL is highly variable. A major determinant of clinical course is the histologic subtype. Most indolent types of NHL are considered to be incurable disease. Patients respond initially to either chemotherapy or antibody therapy and most will relapse. Studies to date have not demonstrated an improvement in survival with early intervention. In asymptomatic patients, it is acceptable to "watch and wait" until the patient becomes symptomatic or the disease pace appears to be accelerating. Over time, the disease may transform to a more aggressive histology. The median survival is 8 to 10 years, and indolent patients often receive 3 or more treatments during the treatment phase of their disease. Initial treatment of the symptomatic indolent NHL patient historically has been combination chemotherapy. The most commonly used agents include: cyclophosphamide, vincristine and prednisone (CVP); or cyclophosphamide, adriamycin, vincristine, prednisone (CHOP). Approximately 70% to 80% of patients will respond to their initial chemotherapy, duration of remissions last on the order of 2-3 years. Ultimately the majority of patients relapse. The discovery and clinical use of the anti-CD20 antibody, rituximab, has provided significant improvements in response and survival rate. The current standard of care for most patients is rituximab+CHOP (R-CHOP) or rituximab+CVP (R-CVP). Interferon is approved for initial treatment of NHL in combination with alkylating agents, but has limited use in the U.S. Rituximab therapy has been shown to be efficacious in several types of NHL, and is currently approved as a first line treatment for both indolent (follicular lymphoma) and aggressive NHL (diffuse large B cell lymphoma). However, there are significant limitations of anti-CD20 monoclonal antibody (mAb), including primary resistance (50% response in relapsed indolent patients), acquired resistance (50% response rate upon re-treatment), rare complete response (2% complete response rate in relapsed population), and a continued pattern of relapse. Finally, many B cells do not express CD20, and thus many B-cell disorders are not treatable using anti-CD20 antibody therapy.

In addition to NHL there are several types of leukemias that result from dysregulation of B cells. Chronic lymphocytic leukemia (also known as "chronic lymphoid leukemia" or "CLL"), is a type of adult leukemia caused by an abnormal accumulation of B lymphocytes. In CLL, the malignant lymphocytes may look normal and mature, but they are not able to cope effectively with infection. CLL is the most common form of leukemia in adults. Men are twice as likely to develop CLL as women. However, the key risk factor is age. Over 75% of new cases are diagnosed in patients over age 50. More than 10,000 cases are diagnosed every year and the mortality is almost 5,000 a year (American Cancer Society, 2006; and SEER Cancer Statistics Review). CLL is an incurable disease but progresses slowly in most cases. Many people with CLL lead normal and active lives for many years. Because of its slow onset, early-stage CLL is generally not treated since it is believed that early CLL intervention does not improve survival time or quality of life. Instead, the condition is monitored over time. Initial CLL treatments vary depending on the exact diagnosis and the progression of the disease. There are dozens of agents used for CLL therapy. Combination chemotherapy regimens such as FCR (fludarabine, cyclophosphamide and rituximab), and BR (Ibrutinib and rituximab) are effective in both newly-diagnosed and relapsed CLL. Allogeneic bone marrow (stem cell) transplantation is rarely used as a first-line treatment for CLL due to its risk.

Another type of leukemia is Small lymphocytic lymphoma (SLL) that is considered a CLL variant that lacks the clonal lymphocytosis required for the CLL diagnosis, but otherwise shares pathological and immunophenotypic features (Campo et al., 2011). The definition of SLL requires the presence of lymphadenopathy and/or splenomegaly. Moreover, the number of B lymphocytes in the peripheral blood should not exceed $5 \times 10^9$/L. In SLL, the diagnosis should be confirmed by histopathologic evaluation of a lymph node biopsy whenever possible (Hallek et al., 2008). The incidence of SLL is approximately 25% of CLL in the US (Dores et al., 2007).

Another type of leukemia is acute lymphoblastic leukemia (ALL), also known as acute lymphocytic leukemia. ALL is characterized by the overproduction and continuous multiplication of malignant and immature white blood cells (also known as lymphoblasts) in the bone marrow. 'Acute' refers to the undifferentiated, immature state of the circulating lymphocytes ("blasts"), and that the disease progresses rapidly with life expectancy of weeks to months if left untreated. ALL is most common in childhood with a peak incidence of 4-5 years of age. Children of age 12-16 die more easily from it than others. Currently, at least 80% of childhood ALL are considered curable. Under 4,000 cases are diagnosed every year and the mortality is almost 1,500 a year (American Cancer Society, 2006; and SEER Cancer Statistics Review).

The use of a CD19 antibody in non-specific B cell lymphomas is discussed in WO2007076950 (US2007154473), which are both incorporated by reference. The use of a CD19 antibody in CLL, NHL and ALL is described in Scheuermann et al., CD19 Antigen in Leukemia and Lymphoma Diagnosis and Immunotherapy, Leukemia and Lymphoma, Vol. 18, 385-397 (1995), which is incorporated by reference in its entirety.

Additional antibodies specific for CD19 are described in WO2005012493 (U.S. Pat. No. 7,109,304), WO2010053716 (U.S. Ser. No. 12/266,999) (Immunomedics); WO2007002223 (U.S. Pat. No. 8,097,703) (Medarex); WO2008022152 (Ser. No. 12/377,251) and WO2008150494 (Xencor), WO2008031056 (U.S. Ser. No. 11/852,106) (Medimmune); WO 2007076950 (U.S. Ser. No. 11/648,505) (Merck Patent GmbH); WO 2009/052431 (U.S. Ser. No. 12/253,895) (Seattle Genetics); and WO2010095031 (Ser. No. 12/710,442) (Glenmark Pharmaceuticals), WO2012010562 and WO2012010561 (International Drug Development), WO2011147834 (Roche Glycart), and WO 2012/156455 (Sanofi), which are all incorporated by reference in their entireties.

The term "CD19" refers to the protein known as CD19, having the following synonyms: B4, B-lymphocyte antigen CD19, B-lymphocyte surface antigen B4, CVID3, Differentiation antigen CD19, MGC12802, and T-cell surface antigen Leu-12.

Human CD19 has the amino acid sequence of:

```
                                            (SEQ ID NO: 7)
MPPPRLLFFLLFLTPMEVRPEEPLVVKVEEGDNAVLQCLKGTSDGPTQQ

LTWSRESPLKPFLKLSLGLPGLGIHMRPLAIWLFIFNVSQQMGGFYLCQ

PGPPSEKAWQPGWTVNVEGSGELFRWNVSDLGGLGCGLKNRSSEGPSSP

SGKLMSPKLYVWAKDRPEIWEGEPPCLPPRDSLNQSLSQDLTMAPGSTL

WLSCGVPPDSVSRGPLSWTHVHPKGPKSLLSLELKDDRPARDMWVMETG

LLLPRATAQDAGKYYCHRGNLTMSFHLEITARPVLWHWLLRTGGWKVSA

VTLAYLIFCLCSLVGILHLQRALVLRRKRKRMTDPIRRFFKVTPPPGSG

PQNQYGNVLSLPTPTSGLGRAQRWAAGLGGTAPSYGNPSSDVQADGALG

SRSPPGVGPEEEEGEGYEEPDSEEDSEFYENDSNLGQDQLSQDGSGYEN

PEDEPLGPEDEDSFSNAESYENEDEELTQPVARTMDFLSPHGSAWDPSR

EATSLGSQSYEDMRGILYAAPQLRSIRGQPGPNHEEDADSYENMDNPDG

PDPAWGGGGRMGTWSTR.
```

"MOR00208" is an anti-CD19 antibody. The amino acid sequence of the variable domains is provided in FIG. 1. The amino acid sequence of the heavy and light chain Fc regions of MOR00208 are provided in FIG. 2. "MOR00208" and "XmAb 5574" are used as synonyms to describe the antibody shown in FIGS. 1 and 2. The MOR00208 antibody is described in U.S. patent application Ser. No. 12/377,251, which is incorporated by reference in its entirety.

U.S. patent application Ser. No. 12/377,251 describes the antibody named 4G7 H1.52 Hybrid S239D/I332E/4G7 L1.155 (later named MOR00208) as follows:

```
>4G7 H1.52 Hybrid S239D/I332E
                                            (SEQ ID NO: 8)
EVQLVESGGGLVKPGGSLKLSCAASGYTFTSYVMHWVRQAPGKGLEWIG

YINPYNDGTKYNEKFQGRVTISSDKSISTAYMELSSLRSEDTAMYYCAR

GTYYYGTRVFDYWGQGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPDVF

LFPPKPKDTLMISRTPEVTCVVVDVSHEDPEVQFNWYVDGVEVHNAKTK

PREEQFNSTFRVVSVLIVVHQDWLNGKEYKCKVSNKALPAPEEKTISKT

KGQPREPQVYTLPPSREEMTKNQVSLTCLVKGFYPSDIAVEWESNGQPE

NNYKTTPPMLDSDGSFFLYSKLTVDKSRWQQGNVFSCSVMHEALHNHYT

QKSLSLSPGK
```

```
-continued
>4G7 L1.155
                                            (SEQ ID NO: 9)
DIVMTQSPATLSLSPGERATLSCRSSKSLQNVNGNTYLYWFQQKPGQSP

QLLIYRMSNLNSGVPDRFSGSGSGTEFTLTISSLEPEDFAVYYCMQHLE

YPITFGAGTKLEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC
```

A pharmaceutical composition includes an active agent, e.g. an antibody for therapeutic use in humans. A pharmaceutical composition may additionally include pharmaceutically acceptable carriers or excipients.

"Administered" or "administration" refers to the delivery of a pharmaceutical composition by an injectable form, such as, for example, an intravenous, intramuscular, intradermal or subcutaneous route or mucosal route, for example, as a nasal spray or aerosol for inhalation or as an ingestable solution, capsule or tablet.

The antibody which is administered according to the present disclosure is administered to the patient in a therapeutically effective amount. A "therapeutically effective amount" refers to an amount sufficient to provide some improvement of the clinical manifestations of a given disease or disorder. As an example, patients in the exemplified study received dosing of MOR00208 at 12 mg/kg once weekly, and in maintenance once every two weeks or monthly.

The amount that is effective for a particular therapeutic purpose will depend on the severity of the disease or injury as well as on the weight and general state of the subject. It will be understood that determination of an appropriate dosage may be achieved, using routine experimentation, by constructing a matrix of values and testing different points in the matrix, all of which is within the ordinary skills of a trained physician or clinical scientist.

Baseline means prior to administration of the desired therapy. For example, prior to administration of the desired anti-CD19 antibody.

A receiver operating characteristic (ROC) analysis was used to analyze the predictivity, sensitivity, specifity and to determine the cut-offs for potential biomarkers, such as NK cell counts, CD16 expression levels on NK cells, and T cells counts. The following additional methods exist for estimating an optimal cut-off: "Max.Accuracy"—the cut-off which maximize the accuracy; b) "Max.DOR"—the cut-off which maximize the diagnostic odds ratio; c) "Error.rate"—the cut-off which minimizes the error rate; d) "Max.Accuracy.area"—the cut-off which maximize the accuracy area; e) "Max.Sens+Spec"—the cut-off which maximize the sum of sensitivity with specificity; f) "Max.Youden"—the cut-off which maximize the Youden index; g) "Se=Sp"—the cut-off which Sensitivity is equal to Specificity; h) "Min.ROC.Dist"—the cut-off which minimize the distance between the curve and the upper left corner of the graph; i) "Max.Efficiency"—the cut-off which maximize the efficiency; and j) "Min.MCT"—the cut-off which minimize the misclassification cost term. See Lopez-Raton, M., Rodriguez-Alvarez, M. X, Cadarso-Suarez, C. and Gude-Sampedro, F. (2014). Optimal Cutpoints: An R Package for Selecting Optimal Cutpoints in Diagnostic Tests. Journal of Statistical Software 61(8), 1-36.

Antibodies specific to CD19 have also been tested preclinically in combination with other drugs. For example, MOR00208 had been tested in combination with nitrogen mustards, purine analogs, thalidomide analogs, phosphoinositide 3-kinase inhibitor, BCL-2 inhibitors and bruton's tyrosine kinase (BTK) inhibitors.

A "nitrogen mustard" is a nonspecific DNA alkylating agent used as chemotherapy. Alkylating agents add an alkyl group (CnH2n+1) to nucleic acid bases, e.g., adding an alkyl group to the guanine base of DNA at the number 7 nitrogen atom of the imidazole ring. The alkylation steps result in the formation of interstrand cross-links (ICLs). These ICLs are highly cytotoxic, since they block fundamental metabolic processes such as replication and transcription. Nitrogen mustards include cyclophosphamide, chlorambucil, uramustine, ifosfamide, melphalan and bendamustine.

Bendamustine is marketed under the names Ribomustin®, and Treanda®, and is also known as SDX-105, by Mundipharma International Corporation Limited (Licensee of Astellas Pharma GmbH) and Cephalon for the treatment of chronic lymphocytic leukemias (CLL), indolent B-cell non-Hodgkin's lymphoma (NHL), and other lymphomas. Bendamustine has the following structure:

A purine analog is an antimetabolite, which mimics the structure of metabolic purines, thereby interfering with the synthesis of nucleic acids. Fludarabine, for example, may be incorporated into RNA and DNA by substituting for the purine nucleotides, adenine and guanine. Purine analogs inhibit growth of fast proliferating cells of an individual, e.g. cancer cells, bone marrow cells or cells present in the gastrointestinal tract. Purine analogs include mercaptopurine, azathioprine, thioguanine and fludarabine. Fludarabine or fludarabine phosphate (Fludara®) is a chemotherapy drug used in the treatment of chronic lymphocytic leukemia and indolent non-Hodgkins lymphomas. Fludarabine is a purine analog. Fludarabine inhibits DNA synthesis by interfering with ribonucleotide reductase and DNA polymerase and is S phase-specific (since these enzymes are highly active during DNA replication). Fludarabine has the following structure:

A "thalidomide analog" includes, but is not limited to, thalidomide itself, lenalidomide (CC-5013, Revlimid™), Pomalidomide (CC4047, Actimid™) and the compounds disclosed in WO2002068414 and WO2005016326, which are incorporated by reference in their entireties. The term refers to a synthetic chemical compound using the thalidomide structure as a backbone (e.g., side groups have been added or such groups have been deleted from the parent structure). The analog differs in structure from thalidomide and its metabolite compounds such as by a difference in the length of an alkyl chain, a molecular fragment, by one or more functional groups, or a change in ionization. The term "thalidomide analog" also includes the metabolites of thalidomide. Thalidomide analogs include the racemic mixture of the S- and the R-enantiomer of a respective compound and the S-enantiomer or to the R-enantiomer individually. The racemic mixture is preferred.

Thalidomide analogs include the compounds of the following structures:

(A) Lenalidomide

A "phosphoinositide 3-kinase inhibitor" is a class of medical drug that functions by inhibiting one or more of the phosphoinositide 3-kinase enzymes, which are part of the PI3K/AKT/mTOR pathway, an important signalling pathway for many cellular functions such as growth control, metabolism and translation initiation.

There are a number of different classes and isoforms of PI3Ks. Class 1 PI3Ks have a catalytic subunit known as p110, with four types (isoforms)—p110 alpha, p110 beta, p110 gamma and p110 delta. Current inhibitors being studied inhibit one or more isoforms of the class I PI3Ks.

Phosphoinositide 3-kinase inhibitors include at least Idelalisib, Duvelisib and Copanlisib. Idelalisib is marketed by Gilead Sciences, Inc. (trade name Zydelig, also named GS-1101 or CAL-101). Idelalisib is is currently labelled for the treatment of relapsed chronic lymphocytic leukemia (CLL), in combination with rituximab, in patients for whom rituximab alone would be considered appropriate therapy due to other co-morbidities; relapsed follicular B-cell non-Hodgkin lymphoma (FL) in patients who have received at least two prior systemic therapies; relapsed small lymphocytic lymphoma (SLL) in patients who have received at least two prior systemic therapies. The substance acts as a phosphoinositide 3-kinase inhibitor; more specifically, it blocks P110δ, the delta isoform of the enzyme phosphoinositide 3-kinase.

The formula of Idelalisib is:

11
12

A "Bruton's tyrosine kinase (BTK) inhibitor" is a class of drug that functions by inhibiting the tyrosine-protein kinase BTK enzyme, which plays an important role in B-cell development. Specifically, BTK contains a PH domain that phenyl)-4,4-dimethyl-1-cyclohexen-1-yl]methyl}-1-piper-azinyl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide and has the following structure:

binds phosphatidylinositol (3,4,5)-trisphosphate (PIP3). PIP3 binding induces Btk to phosphorylate phospholipase C, which in turn hydrolyzes PIP2, a phosphatidylinositol, into two second messengers, inositol triphosphate (IP3) and diacylglycerol (DAG), which then go on to modulate the activity of downstream proteins during B-cell signalling.

Bruton's tyrosine kinase (BTK) inhibitors include Ibrutinib. Ibrutinib is marketed by Pharmacyclics, Inc and Johnson & Johnson's Janssen Pharmaceutical (trade name Imbruvica, also named PCI-32765). Ibrutinib is currently labelled for the treatment of patients with Mantle cell lymphoma (MCL) who have received at least one prior therapy, Chronic lymphocytic leukemia (CLL) who have received at least one prior therapy, Chronic lymphocytic leukemia with 17p deletion, and Waldenström's macro-globulinemia. The formula of Ibrutinib is 1-[(3R)-3-[4-amino-3-(4-phenoxyphenyl)-1H-pyrazolo[3,4-d]pyrimidin-1-yl]-1-piperidinyl]-2-propen-1-one and has the following structure:

A "BCL-2 inhibitor" is a class of drug that functions by inhibiting anti-apoptotic B-cell lymphoma-2 (Bcl-2) protein, leading to programmed cell death of cells. BCL-2 inhibitor include venetoclax. Venetoclax is marketed by Abbvie and Genentech (trade name VENCLEXTA™, also known as GDC-0199, ABT-199, and RG7601). Venetoclax is currently labelled for the treatment of patients with chronic lympho-cytic leukemia (CLL) with 17p deletion, as detected by an FDA approved test, who have received at least one prior therapy. The formula of venetoclax is 4-(4-{[2-(4-Chloro- "Venetoclax," "ABT", and "ABT-199" are used as synonyms herein.

EMBODIMENTS

An aspect is a method of identifying a subject having chronic lymphocytic leukemia (CLL), non-Hodgkin's lymphoma (NHL), acute lymphoblastic leukemia (ALL) or small lymphocytic lymphoma (SLL) that is responsive to treatment with an anti-CD19 antibody, said method comprising:
a. providing a sample obtained from said subject prior to treatment with said anti-CD19 antibody,
b. determining the level of at least one biomarker in said sample selected from the group consisting of:
    i. peripheral NK cell count, and
    ii. CD16 expression levels on peripheral NK cells,
c. comparing the level of said at least one biomarker in said sample to a predetermined cut off level,
    wherein levels of said at least one biomarker at or above the predetermined cut off level is indicative of a subject who would benefit from treatment with an anti-CD19 antibody.

In embodiments, the sample is a blood sample. In embodiments, said sample comprises peripheral NK cells.

In embodiments, the predetermined cut off level of said biomarker is a baseline peripheral NK cell count of at least 50 cells/µl, at least 75 cells/µl, at least 100 cells/µl, at least 125 cells/µl, at least 150 cells/µl, at least 175 cells/µl, at least 200 cells/µl, at least 225 cells/µl, or at least 250 cells/µl. In embodiments, the predetermined cut off level of said bio-marker is baseline CD16 expression levels on peripheral NK cells of at least 45,000 ABCs, at least 60,000 ABCs, at least 75,000 ABCs, or at least 90,000 ABCs.

In embodiments, the predetermined cut off of said bio-marker is:
a. a baseline peripheral NK cell count of at least 50 cells/µl, or
b. baseline CD16 expression levels on peripheral NK cells of at least 60,000 (ABCs).

In embodiments, the predetermined cut of said biomarker is:
a. baseline peripheral NK cell count of at least 50 cells/µl, and b. baseline CD16 expression levels on peripheral NK cells of at least 60,000 (ABCs).

In embodiments, predetermined cut off level a baseline peripheral NK cell count of at least 50 cells/μl. In embodiments, the predetermined cut of said biomarker is baseline CD16 expression levels on peripheral NK cells of at least 60,000 (ABCs).

In embodiments, the predetermined cut off of said biomarker is:

a. a baseline peripheral NK cell count of at least 70 cells/μl, or b. baseline CD16 expression levels on peripheral NK cells of at least 60,000 (ABCs).

In embodiments, the predetermined cut off of said biomarker is:

a. a baseline peripheral NK cell count of at least 70 cells/μl, and b. baseline CD16 expression levels on peripheral NK cells of at least 60,000 (ABCs).

In embodiments, predetermined cut off level a baseline peripheral NK cell count of at least 70 cells/μl. In embodiments, the predetermined cut of said biomarker is baseline CD16 expression levels on peripheral NK cells of at least 60,000 (ABCs).

In embodiments, the predetermined cut off of said biomarker is:

a. a baseline peripheral NK cell count of at least 80 cells/μl, or b. baseline CD16 expression levels on peripheral NK cells of at least 60,000 (ABCs).

In embodiments, the predetermined cut off of said biomarker is:

a. a baseline peripheral NK cell count of at least 80 cells/μl, and b. baseline CD16 expression levels on peripheral NK cells of at least 60,000 (ABCs).

In embodiments, predetermined cut off level a baseline peripheral NK cell count of at least 80 cells/μl. In embodiments, the predetermined cut of said biomarker is baseline CD16 expression levels on peripheral NK cells of at least 60,000 (ABCs).

In embodiments, the predetermined cut off of said biomarker is:

a. a baseline peripheral NK cell count of at least 90 cells/μl, or b. baseline CD16 expression levels on peripheral NK cells of at least 60,000 (ABCs).

In embodiments, the predetermined cut off of said biomarker is:

a. a baseline peripheral NK cell count of at least 90 cells/μl, and b. baseline CD16 expression levels on peripheral NK cells of at least 60,000 (ABCs).

In embodiments, predetermined cut off level a baseline peripheral NK cell count of at least 90 cells/μl. In embodiments, the predetermined cut of said biomarker is baseline CD16 expression levels on peripheral NK cells of at least 60,000 (ABCs).

In embodiments, the predetermined cut off of said biomarker is:

a. a baseline peripheral NK cell count of at least 100 cells/μl, or b. baseline CD16 expression levels on peripheral NK cells of at least 60,000 (ABCs).

In embodiments, the predetermined cut off of said biomarker is:

a. a baseline peripheral NK cell count of at least 100 cells/μl, and b. baseline CD16 expression levels on peripheral NK cells of at least 60,000 (ABCs).

In embodiments, predetermined cut off level a baseline peripheral NK cell count of at least 100 cells/μl. In embodiments, the predetermined cut of said biomarker is baseline CD16 expression levels on peripheral NK cells of at least 60,000 (ABCs).

An aspect is a method of identifying a subject having chronic lymphocytic leukemia (CLL), non-Hodgkin's lymphoma (NHL), acute lymphoblastic leukemia (ALL) or small lymphocytic lymphoma (SLL) that is responsive to treatment with an anti-CD19 antibody, said method comprising:

a. providing a blood sample obtained from said subject prior to treatment with said anti-CD19 antibody, b. determining the level of at least one biomarker in said sample selected from the group consisting of:

i. peripheral NK cell count, and ii. CD16 expression levels on peripheral NK cells, c. comparing the level of said at least one biomarker in said sample to a predetermined cut off level, wherein the baseline peripheral NK cell count is at least 50 cells/μl, at least 60 cells/μl, at least 70 cells/μl, at least 80 cells/μl, at least 90 cells/μl or at least 100 cells/μl and the baseline CD16 expression levels on peripheral NK cells is at least 60,000 (ABCs), and wherein the anti-CD19 antibody comprises an HCDR1 region comprising the sequence SYVMH (SEQ ID NO: 1), an HCDR2 region comprising the sequence NPYNDG (SEQ ID NO: 2), an HCDR3 region comprising the sequence GTYYYGTRVFDY (SEQ ID NO: 3), an LCDR1 region comprising the sequence RSSKSLQNVNGNTYLY (SEQ ID NO: 4), an LCDR2 region comprising the sequence RMSNLNS (SEQ ID NO: 5), and an LCDR3 region comprising the sequence MQHLEYPIT (SEQ ID NO: 6).

An aspect is a method of identifying a subject having chronic lymphocytic leukemia (CLL), non-Hodgkin's lymphoma (NHL), acute lymphoblastic leukemia (ALL) or small lymphocytic lymphoma (SLL) that is responsive to treatment with an anti-CD19 antibody, said method comprising:

a. providing a blood sample obtained from said subject prior to treatment with said anti-CD19 antibody, b. determining the level of at least one biomarker in said sample selected from the group consisting of:

i. peripheral NK cell count, and ii. CD16 expression levels on peripheral NK cells, c. comparing the level of said at least one biomarker in said sample to a predetermined cut off level, wherein the baseline peripheral NK cell count is at least 100 cells/μl, or the baseline CD16 expression levels on peripheral NK cells is at least 60,000 (ABCs), and wherein the anti-CD19 antibody comprises an HCDR1 region comprising the sequence SYVMH (SEQ ID NO: 1), an HCDR2 region comprising the sequence NPYNDG (SEQ ID NO: 2), an HCDR3 region comprising the sequence GTYYYGTRVFDY (SEQ ID NO: 3), an LCDR1 region comprising the sequence RSSKSLQNVNGNTYLY (SEQ ID NO: 4), an LCDR2 region comprising the sequence RMSNLNS (SEQ ID NO: 5), and an LCDR3 region comprising the sequence MQHLEYPIT (SEQ ID NO: 6).

In embodiments, the predetermined cut of said biomarker is:

a. baseline peripheral NK cell count of at least 100 cells/µl, and b. baseline CD16 expression levels on peripheral NK cells of at least 60,000 (ABCs).

In embodiments, the predetermined cut off level of said biomarker is a baseline peripheral NK cell count of at least 50 cells/µl, at least 75 cells/µl, at least 100 cells/µl, at least 125 cells/µl, at least 150 cells/µl, at least 175 cells/µl, at least 200 cells/µl, at least 225 cells/µl, or at least 250 cells/µl. In embodiments, the predetermined cut off level of said biomarker is baseline CD16 expression levels on peripheral NK cells of at least 45,000 ABCs, at least 60,000 ABCs, at least 75,000 ABCs, or at least 90,000 ABCs.

An aspect is a method of treating a patient having chronic lymphocytic leukemia (CLL), non-Hodgkin's lymphoma (NHL), acute lymphoblastic leukemia (ALL) or small lymphocytic lymphoma (SLL) with an anti-CD19 antibody, the method comprising a. obtaining a baseline peripheral NK cell count in the patient, or a baseline CD16 expression level on the peripheral NK cells of the patient, and b. administering an effective amount of the anti-CD19 antibody to the patient having a baseline peripheral NK cell count of at least 50 cells/µl, at least 60 cells/µl, at least 70 cells/µl, at least 80 cells/µl, at least 90 cells/µl or at least 100 cells/µl or a baseline CD16 expression level on the peripheral NK cells of at least 60,000 (ABCs).

An aspect is a method of treating a patient having chronic lymphocytic leukemia (CLL), non-Hodgkin's lymphoma (NHL), acute lymphoblastic leukemia (ALL) or small lymphocytic lymphoma (SLL) with an anti-CD19 antibody, the method comprising a. obtaining a baseline peripheral NK cell count in the patient, or a baseline CD16 expression level on the peripheral NK cells of the patient, and b. administering an effective amount of the anti-CD19 antibody to the patient having a baseline peripheral NK cell count of at least 100 cells/µl or a baseline CD16 expression level on the peripheral NK cells of at least 60,000 (ABCs).

In embodiments, the method of treating a patient chronic lymphocytic leukemia (CLL), non-Hodgkin's lymphoma (NHL), acute lymphoblastic leukemia (ALL) or small lymphocytic lymphoma (SLL) with an anti-CD19 antibody, comprises a. obtaining an baseline peripheral NK cell count in the patient, and b. administering an effective amount of the anti-CD19 antibody to the patient having an NK cell count of at least 50 cells/µl, at least 60 cells/µl, at least 70 cells/µl, at least 80 cells/µl, at least 90 cells/µl or at least 100 cells/µl.

In embodiments, the method of treating a patient chronic lymphocytic leukemia (CLL), non-Hodgkin's lymphoma (NHL), acute lymphoblastic leukemia (ALL) or small lymphocytic lymphoma (SLL) with an anti-CD19 antibody, comprises a. obtaining an baseline peripheral NK cell count in the patient, and b. administering an effective amount of the anti-CD19 antibody to the patient having an NK cell count of at least 50 cells/µl, at least 60 cells/µl, at least 70 cells/µl, at least 80 cells/µl, at least 90 cells/µl or at least 100 cells/µl.

In embodiments, the method of treating a patient chronic lymphocytic leukemia (CLL), non-Hodgkin's lymphoma (NHL), acute lymphoblastic leukemia (ALL) or small lymphocytic lymphoma (SLL) with an anti-CD19 antibody, comprises a. obtaining an baseline peripheral NK cell count in the patient, and b. administering an effective amount of the anti-CD19 antibody to the patient having an NK cell count of at least 100 cells/µl.

In embodiments, the method of treating a patient having chronic lymphocytic leukemia (CLL), non-Hodgkin's lymphoma (NHL), acute lymphoblastic leukemia (ALL) or small lymphocytic lymphoma (SLL) with an anti-CD19 antibody, comprises a. obtaining baseline CD16 expression levels on the peripheral NK cells of the patient, and b. administering an effective amount of the anti-CD19 antibody to the patient having CD16 levels on the NK cells of at least 60,000 (ABCs).

In embodiments, the anti-CD19 antibody is administered to patients having both a baseline peripheral NK cell count of of at least 50 cells/µl, at least 60 cells/µl, at least 70 cells/µl, at least 80 cells/µl, at least 90 cells/µl or at least 100 cells/µl, and a baseline CD16 expression level on peripheral NK cells of at least 60,000 (ABCs).

In embodiments, the anti-CD19 antibody is administered to patients having both a baseline peripheral NK cell count of at least 100 cells/µl, and a baseline CD16 expression level on peripheral NK cells of at least 60,000 (ABCs).

In embodiments, the anti-CD19 antibody is administered to patients having a baseline peripheral NK cell count of at least 50 cells/µl, at least 75 cells/µl, at least 100 cells/µl, at least 125 cells/µl, at least 150 cells/µl, at least 175 cells/µl, at least 200 cells/µl, at least 225 cells/µl, or at least 250 cells/µl. In embodiments, the anti-CD19 antibody is administered to patients having baseline CD16 expression levels on peripheral NK cells of at least 45,000 ABCs, at least 60,000 ABCs, at least 75,000 ABCs, or at least 90,000 ABCs.

An aspect is a method of treating a patient having chronic lymphocytic leukemia (CLL), non-Hodgkin's lymphoma (NHL), acute lymphoblastic leukemia (ALL) or small lymphocytic lymphoma (SLL) with an anti-CD19 antibody, said method comprising:

a. providing a sample obtained from said subject prior to treatment with said anti-CD19 antibody, b. determining the level of at least one biomarker in said sample selected from the group consisting of:

i. peripheral NK cell count, and ii. CD16 expression levels on peripheral NK cells, c. comparing the level of said at least one biomarker in said sample to a predetermined cut off level, d. administering an effective amount of anti-CD19 antibody to the patient having an peripheral NK cell count of at least 100 cells/µl or CD16 expression level on the peripheral NK cells of at least 60,000 (ABCs).

An aspect is a method of treating a patient having chronic lymphocytic leukemia (CLL), non-Hodgkin's lymphoma (NHL), acute lymphoblastic leukemia (ALL) or small lymphocytic lymphoma (SLL) comprising administering an effective amount of an anti-CD19 antibody to the patient if a. the baseline peripheral NK cell count of the patient is at least 100 cells/µl or b. the baseline CD16 expression levels on peripheral NK cells is at least 60,000 (ABCs).

An aspect is a method of treating a patient having chronic lymphocytic leukemia (CLL), non-Hodgkin's lymphoma (NHL), acute lymphoblastic leukemia (ALL) or small lymphocytic lymphoma (SLL) comprising a. obtaining the peripheral NK cell count of the patient, b. administering an effective amount of an anti-CD19 antibody to patients having peripheral NK cell counts of at least 100 cells/µl.

An aspect is a method of treating a patient having chronic lymphocytic leukemia (CLL), non-Hodgkin's lymphoma (NHL), acute lymphoblastic leukemia (ALL) or small lymphocytic lymphoma (SLL) comprising a. obtaining the CD16 expression levels on the peripheral NK cells of the patient, b. administering an effective amount of an anti-CD19 antibody to patients having an CD16 expression levels on the peripheral NK cells of at least 60,000 (ABCs).

In embodiments, anti-CD19 antibody is administered to patients having both a baseline peripheral NK cell count of at least 100 cells/µl, and a baseline CD16 expression level on peripheral NK cells of at least 60,000 (ABCs). In embodiments, the anti-CD19 antibody is administered to patients having a baseline peripheral NK cell count of at least 50 cells/µl, at least 75 cells/µl, at least 100 cells/µl, at least 125 cells/µl, at least 150 cells/µl, at least 175 cells/µl, at least 200 cells/µl, at least 225 cells/µl, or at least 250 cells/µl. In embodiments, the anti-CD19 antibody is administered to patients having baseline CD16 expression levels on peripheral NK cells of at least 45,000 ABCs, at least 60,000 ABCs, at least 75,000 ABCs, or at least 90,000 ABCs.

In embodiments the baseline peripheral NK cell count or baseline CD16 levels (ABCs) on the peripheral NK cells is obtained from a blood sample taken from the patient. In embodiments the peripheral NK cell count and/or the CD16 expression levels are measured prior to administration of the anti-CD19 antibody.

In embodiments, the antibody specific for CD19 comprises an HCDR1 region comprising the sequence SYVMH (SEQ ID NO: 1), an HCDR2 region comprising the sequence NPYNDG (SEQ ID NO: 2), an HCDR3 region comprising the sequence GTYYYGTRVFDY (SEQ ID NO: 3), an LCDR1 region comprising the sequence RSSKSLQNVNGNTYLY (SEQ ID NO: 4), an LCDR2 region comprising the sequence RMSNLNS (SEQ ID NO: 5), and an LCDR3 region comprising the sequence MQHLEYPIT (SEQ ID NO: 6).

In embodiments the baseline peripheral NK cell count or baseline CD16 expression levels on the peripheral NK cells is obtained from a blood sample taken from the patient.

In an embodiment, the patient has non-Hodgkin's lymphoma. In embodiments, the non-Hodgkin's lymphoma is selected from the group consisting of follicular lymphoma, small lymphocytic lymphoma, mucosa-associated lymphoid tissue, marginal zone, diffuse large B cell, Burkitt's, and mantle cell. In an embodiment, the non-Hodgkin's lymphoma is follicular lymphoma. In an embodiment, the non-Hodgkin's lymphoma is indolent non-Hodgkin's lymphoma. In an embodiment, the non-Hodgkin's lymphoma is small lymphocytic lymphoma. In an embodiment, the non-Hodgkin's lymphoma is mucosa-associated lymphoid tissue. In an embodiment, the non-Hodgkin's lymphoma is marginal zone lymphoma. In an embodiment, the non-Hodgkin's lymphoma is diffuse large B cell lymphoma. In an embodiment, the non-Hodgkin's lymphoma is Burkitt's lymphoma. In an embodiment, the non-Hodgkin's lymphoma is mantle cell lymphoma. In an embodiment, the patient has chronic lymphocytic leukemia. In an embodiment, the patient has acute lymphoblastic leukemia. In an embodiment, the patient has small lymphocytic lymphoma (SLL).

In embodiments, the treatment results in the therapeutic effect selected from the group consisting of Disease Control Rate (DCR) and longer duration of Progression Free Survival.

In embodiments, the treatment further comprises administration of an effective amount of a nitrogen mustard. In an embodiment that nitrogen mustard is bendamustine. In embodiments, the treatment further comprises administration of an effective amount of a purine analog. In embodiments, the purine analog is fludarabine. In embodiments, the treatment further comprises administration of an effective amount of a Bruton's tyrosine kinase (BTK) inhibitor. In embodiments, the Bruton's tyrosine kinase (BTK) inhibitor is ibrutinib. In embodiments, the treatment further comprises administration of an effective amount of a phosphoinositide 3-kinase inhibitor. In an embodiment the phosphoinositide 3-kinase inhibitor is idelalisib. In embodiments, the treatment further comprises administration of an effective amount of a thalidomide analog. In an embodiment, the thalidomide analog is lenalidomide. In embodiments, the treatment further comprises administration of an effective amount of a BCL-2 inhibitor. In an embodiment, the BCL-2 inhibitor is venetoclax.

As the exemplified anti-CD19 antibody and other anti-CD19 antibodies bind CD19, it is believed that similar results may be seen with other anti-CD19 antibodies. Other anti-CD19 antibodies are described in U.S. patent application Ser. No. 12/377,251 (Xencor), WO2005012493, WO2010053716 (Immunomedics); WO2007002223 (Medarex); WO2008022152 (Xencor); WO2008031056 (Medimmune); WO 2007/076950 (Merck Patent GmbH); WO 2009/052431 (Seattle Genetics); and WO2010095031 (Glenmark Pharmaceuticals), all of which are incorporated by reference in their entireties.

In embodiments, the antibody specific for CD19 comprises an antibody that cross-competes with the antibody comprising an HCDR1 region comprising the sequence SYVMH (SEQ ID NO: 1), an HCDR2 region comprising the sequence NPYNDG (SEQ ID NO: 2), an HCDR3 region comprising the sequence GTYYYGTRVFDY (SEQ ID NO: 3), an LCDR1 region comprising the sequence RSSKSLQNVNGNTYLY (SEQ ID NO: 4), an LCDR2 region comprising the sequence RMSNLNS (SEQ ID NO: 5), and an LCDR3 region comprising the sequence MQHLEYPIT (SEQ ID NO: 6).

In embodiments, the antibody specific for CD19 comprises an antibody that binds to the same epitope as an antibody comprising an HCDR1 region comprising the sequence SYVMH (SEQ ID NO: 1), an HCDR2 region comprising the sequence NPYNDG (SEQ ID NO: 2), an HCDR3 region comprising the sequence GTYYYGTRVFDY (SEQ ID NO: 3), an LCDR1 region comprising the sequence RSSKSLQNVNGNTYLY (SEQ ID NO: 4), an LCDR2 region comprising the sequence RMSNLNS (SEQ ID NO: 5), and an LCDR3 region comprising the sequence MQHLEYPIT (SEQ ID NO: 6).

In embodiments, the antibody specific for CD19 comprises an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6).

In embodiments, the antibody specific for CD19 comprises a variable heavy chain of the sequence

```
                                    (SEQ ID NO: 10)
EVQLVESGGGLVKPGGSLKLSCAASGYTFTSYVMHWVRQAPGKGLEWIG
YINPYNDGTKYNEKFQGRVTISSDKSISTAYMELSSLRSEDTAMYYCAR
GTYYYGTRVFDYWGQGTLVTVSS
and a variable light chain of the sequence
                                    (SEQ ID NO: 11)
DIVMTQSPATLSLSPGERATLSCRSSKSLQNVNGNTYLYWFQQKPGQSP
QLLIYRMSNLNSGVPDRFSGSGSGTEFTLTISSLEPEDFAVYYCMQHLE
YPITFGAGTKLEIK.
```

In an embodiment said antibody comprises a heavy chain constant domain of the sequence

```
                                    (SEQ ID NO: 12)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGGPDVFLFPPKPKDTLMISRTPEVTCVVV

DVSHEDPEVQFNWYVDGVEVHNAKTKPREEQFNSTFRVVSVLTVVHQDW

LNGKEYKCKVSNKALPAPEEKTISKTKGQPREPQVYTLPPSREEMTKNQ

VSLTCLVKGFYPSDIAVEWESNGQPENNYKTTPPMLDSDGSFFLYSKLT

VDKSRWQQGNVFSCSVMHEALHNHYTQKSLSLSPGK.
```

In an embodiment, the antibody specific for CD19 comprises a light chain constant domain of the sequence

```
                                    (SEQ ID NO: 13)
RTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPV
TKSFNRGEC.
```

In an embodiment, the antibody specific for CD19 comprises a heavy chain having the sequence

```
                                    (SEQ ID NO: 8)
EVQLVESGGGLVKPGGSLKLSCAASGYTFTSYVMHWVRQAPGKGLEWIG

YINPYNDGTKYNEKFQGRVTISSDKSISTAYMELSSLRSEDTAMYYCAR

GTYYYGTRVFDYWGQGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPDVF

LFPPKPKDTLMISRTPEVTCVVVDVSHEDPEVQFNWYVDGVEVHNAKTK

PREEQFNSTFRVVSVLTWHQDWLNGKEYKCKVSNKALPAPEEKTISKTK

GQPREPQVYTLPPSREEMTKNQVSLTCLVKGFYPSDIAVEWESNGQPEN

NYKTTPPMLDSDGSFFLYSKLIVDKSRWQQGNVFSCSVMHEALHNHYTQ

KSLSLSPGK
```

In an embodiment, the antibody specific for CD19 comprises a light chain having the sequence

```
                                    (SEQ ID NO: 9)
DIVMTQSPATLSLSPGERATLSCRSSKSLQNVNGNTYLYWFQQKPGQSP

QLLIYRMSNLNSGVPDRFSGSGSGTEFTLTISSLEPEDFAVYYCMQHLE
```

```
                      -continued
YPITFGAGTKLEIKRTVAAPSVF1FPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC.
```

Embodiments comprise a pharmaceutical composition. In embodiments, the composition comprises an acceptable carrier. In embodiments, the composition is administered in an effective amount.

EXAMPLES

Example 1: T Cell and NK Cell Counting

The scope of the MOR00208C201 clinical study included the assessment of several exploratory biomarkers. As part of this initiative baseline peripheral T and NK cell counting was performed at the clinical sites.

T cells are a type of lymphocyte (a subtype of white blood cell) that play a central role in cell-mediated immunity. They can be distinguished from other lymphocytes, such as B cells and NK cells, by the presence of a T-cell receptor on the cell surface.

Natural killer cells or NK cells are a type of cytotoxic lymphocyte critical to the innate immune system. NK cells provide rapid responses to viral-infected cells, acting at around 3 days after infection, and respond to tumor formation. Typically, immune cells detect major histocompatibility complex (MHC) presented on infected cell surfaces, triggering cytokine release, causing lysis or apoptosis. NK cells are unique, however, as they have the ability to recognize stressed cells in the absence of antibodies and MHC, allowing for a much faster immune reaction.

Materials and Methods

TriTest CD3 FITC/CD16+CD56 PE/CD45 PerCP (with Tru-COUNT tubes), BD Biosciences, Cat: 340403 (US); 342442 (Europe). Pipettors and pipet tips capable of delivering 20 μL, 50 μL and 450 μL, Gilson Inc. FACS Lysing Solutions, BD Biosciences, Cat: 349202.

Instruments: Flow cytometer, Vortex

Background of Flow Cytometry:

Whole blood is stained with fluorochrome-labeled antibodies (TriTEST reagents) that bind specifically to leucocyte surface antigens. The cells travel past the laser beam and scatter the laser light. The stained cells fluoresce. These scatter and fluorescence signals, detected by the instrument, provide information about the cell's size, internal complexity, and relative fluorescence intensity. TriTEST reagents employ fluorescence triggering, allowing direct fluorescence gating of the NK- and T-cell lymphocyte population to reduce contamination of unlysed or nucleated red blood cells in the gate.

Staining

For each patient sample, a TruCOUNT Tube was labelled with the sample identification number. 20 μL of TriTEST CD3/CD16+CD56/CD45 reagent was pipetted into the bottom of the tube. 50 μL of well-mixed, anticoagulated whole blood was pipetted into the bottom of the tube. Anticoagulated blood (EDTA) stored at room temperature (20-25° C.) must be stained within 24 hours of draw and analyzed within 6 hours of staining (keep at room temperature and protected from light). The tube was vortexed gently to mix. The tube was incubated for 15 minutes in the dark at room temperature (20-25° C.). 450 μL 1X FACS Lysing Solution was added to the tube. The tube was vortexed and incubated again for 15 minutes in the dark at room temperature (20-25° C.).

Using TruCOUNT Tubes, a known volume of sample is stained directly in a TruCOUNT Tube. The lyophilized pellet in the tube dissolves, releasing a known number of fluorescent beads. During analysis, the absolute number (cells/µL) of positive cells in the sample can be determined by comparing cellular events to bead events.

Flow Cytometry

The cells were vortexed thoroughly (at low speed) to reduce aggregation before running them on the flow cytometer.

Data Analyses

The CD45 vs SSC dot plot was visually inspected. Lymphocytes appear as a bright, compact cell population with low to moderate SSC. Monocytes (M) and granulocytes (G) appear as distinct populations. Analysis was completed when the cell populations of monocytes and lymphocytes showed clear separation.

Lymphocytes were first gated as CD45 positive, low SSC cell population. CD16/CD56 vs CD3 were pre-selected. T-cells (T) should appear as a compact bright CD3 positive cluster. NK-cells (NK) should appear as a compact bright CD16/CD56 positive cluster. Gating was completed and the T, and NK cells were counted.

Bead event counts were done using a CD16/CD56 vs CD3 plot without any pre-selected gate. Beads should appear as a PE/FITC double positive cluster.

Calculating Absolute Counts

The absolute number (cells/µL blood) of T cells or NK cells in the sample was determined by comparing cellular events to bead events. Either MultiSET software or manual (using CellQuest or other software) data analysis was done. For manual counting, the number (#) of positive cellular acquired events was divided by the number (#) of acquired bead events, then multiplied by the (total TruCOUNT bead count (lot dependent) divided by whole blood sample volume of 50 µL). The result is absolute cell numbers per microliter.

Equation:

$$\frac{\text{number of events in gate}}{\substack{\text{containing cell population} \\ (T \text{ or } NK)}} \times \frac{\text{# of total } TruCOUNT \text{ beads}}{50 \text{ µl whole blood}} =$$
$$\text{number of events in gate 2}$$
$$\text{containing bead population}$$

$$= \text{ # cells/µl blood}$$

Example:

$$\frac{2709 \text{ acquired } T\text{–cells}}{10000 \text{ acquired beads}} \times \frac{51667 \text{ total beads in tube}}{50 \text{ µl}} = 280 \ T\text{–cells/µl blood}$$

Example 2: CD16 Quantification on NK Cells

As part of MOR00208C201 clinical study, CD16 (an exploratory biomarker) was quanitified on peripheral NK Cells centrally by ICON Central Laboratories (Farmingdale, New York).

Materials and Methods

Antibodies: CD45 AmCyan (Clone 2D1, BD Biosciences, Cat #339192); CD3 FITC (Clone UCHT1, BioLegend, Cat #300406); Mouse IgG FITC (Clone MOPC-21, BioLegend, Cat #400110); CD16 PE (Clone 3G8, BioLegend, Cat #302008); MOR00208; Mouse IgG PE (Clone MOPC-21, BioLegend, Cat #400114); CD56 PerCP-Cy5.5 (Clone HCD56, BioLegend, Cat #318322); and Mouse IgG PerCP-Cy5.5 (Clone MOPC-21, BioLegend, Cat #400150).

Material: PharmaTherm insulated shippers (Intelsius, Catalog #PHT014); BD Vacutainer® CPT™ Mononuclear Cell Preparation Tube—Sodium Heparin (16×125 mm/8 mL) (BD, Catalog #362753); BD Falcon™ 12×75 mm round-bottom tubes (BD, Catalog #352052); CS&T Beads (BD Biosciences Cat #642212); Fetal Bovine Serum (FBS), heat inactivated (Sigma F4135, or equivalent); Dulbecco's PBS without $Ca^{++}$ and $Mg^{++}$ (Gibco, Cat #14190, or equivalent); BD Falcon, Cell Strainer, 100 µm, yellow (BD Bioscience, Cat #352360); FACS Buffer, 3% of heat inactivated FBS in 1X DPBS; Deionized water, laboratory stock; Crushed (wet) ice; Ice bucket; Aluminum foil; Conical Tubes, 50 mL; Conical Tubes, 15 mL; Sterile, filter pipette tips; BD Pharm Lyse Lysing Buffer (BD Biosciences, Cat #555899); ViViD LIVE/DEAD® Fixable Violet Dead Cell Stain Kit, for 405 nm excitation (Life Technologies, Cat #L34955); ArC Amine Reactive Beads (Life Technologies, Cat #A10346); BD QuantiBRITE Beads (BD Biosciences, Cat #340495); and 52 µm nylon mesh (Miami Aqua Culture, for Cat: Nylon 52 µm, 32% open area woven into material).

Equipment: Centrifuge (refrigerated capability); Lab quake (Tube rocker); Vortex mixer; Laminar flow hood; Incubator (Set at 37° C., 5% $CO_2$); Advia (cell counter); BD FACSCANTO II flow cytometer; Desi-Vac™ Container, 1.5 liters (VWR, Cat #62344-930); Humidity Sponge™ Indicating (VWR, Cat #61161-319); and Traceable Humidity-On-A-Card (VWR, Cat #15551-012).

TABLE 1

| CD16 Quantification Assay Panel for PBMC (Peripheral Blood Mononuclear Cell) | | | | | | | |
|---|---|---|---|---|---|---|---|
| Description | Tube # | V450 | AmCyan | FITC | PE | PerCP-Cy5.5 | APC |
| Control Tube I | 1 | ViViD | CD45 | Ms IgG | Ms IgG | Ms IgG | — |
| CD16 ABC | 2 | ViViD | CD45 | CD3 | CD16 | CD56 | — |

PBMC Preparation and Labeling Procedures

Patient's peripheral blood was collected in a CPT tubes and shipped overnight from clinical sites to the central lab in insulated shippers. CPT tubes were centrifuged for 25 min at 1800×g at RT with brake ON. After centrifugation, CPT tubes were immediately inverted and placed for 10 min on the lab quake to resuspend PBMC layer in autologous plasma and resolve majority of formed cell aggregates. Under sterile conditions, homogenized PBMC/plasma suspension was decanted slowly into the center of 100 µm cell strainer resting on top of a sterile 50 mL conical tube. An equal volume of 1X DPBS was added to the PBMC/plasma suspension (approximately 4 mL) in 15 mL conical tube. The tubes were centrifuged at 300×g for 10 min at 4° C. and supernatant removed. The tubes were vortexed to resuspend cell pellet. The cell pellet was washed with DBPS, centrifuged, supernatant removed and resuspended by vortexing. The washed PBMC suspension was added into an eppendorf tube containing 1 µL ViViD stock solution; incubated for 15 min on ice and kept in dark (cover with aluminum foil). The stained ViViD PBMC were transferred into a new labeled conical tube and then ice cold FACS Buffer was added. The cells were centrifuged and vortexed again for resuspension. Polystyrene falcon tubes were labeled for each sample (Table 1). The antibodies or isotype control antibodies were added to the appropriate tubes. The aliquot of ViViD stained PBMCs was added to each tube (Table 1). The tubes were vortexed and incubate. FACS Buffer was added and the cells were centrifuged and vortexed again for resuspension. BD Pharm Lyse Lysing Buffer was added, and the cells were vortexed, centrifuge and aspirated to remove supernatant and vortexed again to resuspend. FACS Buffer was added again and the cells were centrifuged and vortexed again for resuspension. Samples were then acquired on the FACSCanto II Cytometer and ABCs (Antibodies Bound Per Cell) were estimated from standardized MFI as described in Iyer S, et al., Expression of CD69 on activated T cells using R-phycoerythrin labeled beads, Cytometry, 1996; #AC78 (Suppl. 8):113 and Iyer S., et al., QuantiBRITE: A New Standard for Fluorescence Quantitation, Becton Dickinson Immunocytometry Systems, San Jose, CA. 1997. White Paper.

Example 3: NHL Trial

The study of Fc-Optimized Anti-CD19 Antibody (MOR00208) to Treat Non-Hodgkin's Lymphoma (NHL) ClinicalTrials.gov Identifier: NCT01685008 is no longer recruiting.

The Inclusion Criteria were as follows:

1. Male or female patients ≥18 years of age.
2. Histologically-confirmed diagnosis according to REAL/WHO classification, of the following B-cell lymphomas: a.FL, b.MCL, c.DLBCL, d.Other indolent NHL (eg, MZL/MALT).
3. Patients' NHL must have progressed after at least 1 prior rituximab containing regimen.
4. One site of measurable disease by magnetic resonance imaging (MRI) or computed tomography (CT) scan defined as at least one lesion that measures at least 1.5×1.5 cm, with the exception: For patients with MCL only, patients with nonmeasurable disease but evaluable sites (bone marrow, spleen, peripheral blood, gastrointestinal tract) can be enrolled.
5. Patients who have previously received an autologous stem cell transplantation must be at least 4 weeks post-transplant before study drug administration and must have exhibited a full haematological recovery.
6. Discontinued previous monoclonal antibody therapy (except rituximab) or radioimmunotherapy administration for at least 60 days before study drug administration.
7. Off rituximab for at least 14 days before the screening visit and be confirmed to have either no response or have disease progression after rituximab treatment.
8. Patients with DLBCL had a positive [18F]fluorodeoxyglucose-positron emission tomography (FDG-PET) scan at baseline (Cheson response criteria).
9. Life expectancy of >3 months.
10. ECOG performance status of <3.
11. Laboratory criteria at screening: a) Absolute neutrophil count (ANC) ≥1.0 (1000/mm3) b) Platelet count ≥75×109/L without previous transfusion within 10 days of first study drug administration. c) Haemoglobin ≥8.0 g/dL (may have been transfused). d) Serum creatinine <2.0×upper limit of normal (ULN). e) Total bilirubin ≤2.0×ULN. f) Alanine transaminase (ALT) and aspartate aminotransferase (AST) ≤2.5×ULN.

12. If a female of childbearing potential, a negative pregnancy test must be confirmed before enrollment and use of double-barrier contraception, oral contraceptive plus barrier contraceptive, or confirmation of having undergone clinically documented total hysterectomy and/or oophorectomy, tubal ligation.
13. If a male, an effective barrier method of contraception must be used during the study and for 3 months after the last dose if the patient is sexually active with a female of childbearing potential.
14. Able to comply with all study-related procedures, medication use, and evaluations.
15. Able understand and give written informed consent and comply with the study protocol.

The Exclusion Criteria were as follows:

1. Previous treatment with cytotoxic chemotherapy, immunotherapy, radiotherapy or other lymphoma specific therapy within 14 days before the screening visit or patient has not recovered from side effects of previous lymphoma-specific therapy.
2. Treatment with a systemic investigational agent within 28 days before the screening visit.
3. Previous treatment with an anti-CD19 antibody or fragments.
4. Previous allogenic stem cell transplantation.
5. Known or suspected hypersensitivity to the excipients contained in the study drug formulation.
6. Clinically significant cardiovascular disease or cardiac insufficiency, cardiomyopathy, preexisting clinically significant arrhythmia, acute myocardial infarction within 3 months of enrollment, angina pectoris within 3 months of enrollment.
7. Clinical or laboratory evidence of active hepatitis B or hepatitis C.
8. History of HIV infection.
9. Any active systemic infection (viral, fungal, or bacterial) requiring active parenteral antibiotic therapy within 4 weeks of study drug administration.
10. Current treatment with immunosuppressive agents other than prescribed corticosteroids (not more than 10-mg prednisone equivalent).
11. Major surgery or radiation therapy within 4 weeks before first study drug administration.
12. Systemic diseases (cardiovascular, renal, hepatic, etc) that would prevent study treatment in the investigator's opinion.
13. History or clinical evidence of central nervous system (CNS), meningeal, or epidural disease, including brain metastasis.
14. Active treatment/chemotherapy for another primary malignancy within the past 5 years.
15. Pregnancy or breastfeeding in women and women of childbearing potential not using an acceptable method of birth control.
16. History of noncompliance to medical regimens or patients who are considered potentially unreliable not cooperative.

Patients were treated with MOR00208 as follows. Patients were treated with two 28 day cycles, where MOR00208 was given at a dose of 12 mg/kg on days 1, 8, 15, and 22. At the end of the two cycles, patients having Stable Disease or better were treated with a third 28 day cycle applying the same dosing and schedule as the first two cycles. At the end of the third cycle, patients having Partial Response or better went into Maintenance. In Maintenance, MOR00208 was given at a dose of 12 mg/kg every 14 or 28 days until disease progression.

As of the end of the study, the patient characteristics were as follows:

TABLE 2

Baseline characteristics

| Characteristic | | DLBCL n = 35 | iNHL n = 45 | MCL n = 12 | Total n = 92 |
|---|---|---|---|---|---|
| Age, years | Median | 71 | 66 | 64.5 | 66.5 |
| Sex | Male | 24 (69) | 21 (47) | 11 (92) | 56 (61) |
| ECOG PS | 0 | 20 (57) | 33 (73) | 7 (58) | 60 (65) |
| | 1 | 12 (34) | 11 (24) | 4 (33) | 27 (29) |
| | 2 | 3 (9) | 1 (2) | 1 (8) | 5 (5) |
| Rituximab refractory | Yes | 24 (69) | 22 (49) | 6 (50) | 52 (57) |
| | No | 11 (31) | 23 (51) | 6 (50) | 40 (43) |
| Last rituximab dose | <6 mos | 14 (40) | 6 (13) | 1 (8) | 21 (23) |
| Prior stem cell transplant | Yes | 2 (6) | 7 (16) | 1 (8) | 10 (11) |
| DoR to last prior therapy | >12 months | 3 (9) | 18 (40) | 4 (33) | 25 (27) |
| | ≤12 months | 26 (74) | 25 (56) | 7 (58) | 58 (63) |
| | Unknown | 6 (17) | 2 (4) | 1 (8) | 9 (10) |
| Baseline NK cell count | >100 cells/μl | 19 (54) | 23 (51) | 8 (67) | 51 (55) |
| | ≤100 cells/μl | 11 (31) | 8 (18) | 1 (8) | 20 (22) |
| | Unknown | 5 (14) | 14 (31) | 3 (25) | 21 (23) |
| Baseline CD16 expression on NK cells | >60000 ABCs | 15 (43) | 33 (73) | 5 (42) | 53 (58) |
| | ≤60000 ABCs | 11 (31) | 5 (11) | 4 (33) | 20 (22) |
| | Unknown | 9 (26) | 7 (16) | 3 (25) | 19 (21) |
| Baseline T cell count | >500 cells/μl | 20 (57) | 26 (58) | 8 (67) | 54 (59) |
| | ≤500 cells/μl | 10 (29) | 6 (13) | 1 (8) | 17 (18) |
| | Unknown | 5 (14) | 13 (29) | 3 (25) | 21 (23) |
| FcyRIIIa | High affinity | 5 (14) | 4 (9) | 1 (8) | 10 (11) |
| | Low affinity | 27 (77) | 28 (62) | 9 (57) | 64 (70) |
| | Unknown | 3 (9) | 13 (29) | 2 (17) | 18 (20) |
| FcyRIIa | High affinity | 11 (31) | 10 (22) | 3 (25) | 24 (26) |
| | Low affinity | 21 (60) | 22 (49) | 7(58) | 50 (54) |
| | Unknown | 3 (9) | 13 (29) | 2 (17) | 18 (18) |

DLBCL, diffuse large B-cell lymphoma; ECOG PS, Eastern Cooperative Oncology Group performance status; iNHL, indolent non-Hodgkin's lymphoma (includes follicular lymphoma and other iNHL); MCL, mantle cell lymphoma; mos, months. (%)

Other iNHL means a heterogeneous group of not further specified indolent, not aggressive, NHL types, e.g. Marginal Cell Lymphoma, Marginal Zone Lymphoma, and Mucosa associated lymphoid tissue (MALT) lymphoma.

The Key primary and secondary endpoints were as follows:

Primary: Overall Response Rate (ORR)=CR+PR

Secondary:

Disease Control Rate (DCR)=CR+PR+SD

Progression-free survival (PFS)

TABLE 3

Response

| Best overall response,* n (%) | DLBCL n = 35 | iNHL[†] n = 45 | MCL n = 12 | Total n = 92 |
|---|---|---|---|---|
| Complete response, CR | 2 (6) | 5 (11) | 0 | 7 (8) |
| Partial response, PR | 7 (20) | 8 (18) | 0 | 15 (16) |
| Stable disease, SD | 5 (14) | 20 (44) | 6 (50) | 31 (34) |
| Progressive disease | 11 (31) | 7 (16) | 5 (42) | 23 (25) |
| Not evaluable[‡] | 10 (29) | 5 (11) | 1 (8) | 16 (17) |
| DCR (CR + PR + SD) | 14 (40) | 33 (73) | 6 (50) | 53 (58) |
| ORR (CR + PR/all patients) | 9 (26) | 13 (29) | 0 | 22 (24) |
| ORR (CR + PR/ evaluable patients[§]) | 9 (36) | 13 (33) | 0 | 22 (29) |

Data are n (%). *Investigator assessed. †Includes follicular lymphoma and other indolent NHLs. ‡Post-baseline response assessment not performed/data unavailable. §n=25, 40, 11 and 76, respectively. DCR, disease control rate; DLBCL, diffuse large B-cell lymphoma; iNHL, indolent non-Hodgkin's lymphoma; MCL, mantel cell lymphoma' ORR, overall response rate.

The response criteria in this study are those as defined in Table 4. All of them are based on the International Working Group Response Criteria (2007).

TABLE 4

Response Criteria

| Response | Definition | Nodal masses | Spleen, liver | Bone marrow |
|---|---|---|---|---|
| CR | Disappearance of all evidence of disease | a) FDG-avid or PET positive prior to therapy; mass of any size permitted if PET negative b) Variable FDG-avid or PET negative; regression to normal size on CT | Not palpable, nodules disappeared | Infiltrate cleared on repeat biopsy; if in determinate by morphology, immuno-histochemistry should be negative |
| PR | Regression of measurable disease and no new sites | ≥50% decrease in SPD of up to 6 largest dominant masses; no increase in size on CT a) FDG-avid or PET positive prior to therapy; one or more PET positive at previously involved site b) Variable FDG-avid or PET negative; regression on CT | ≥50% decrease in SPD of nodules (for single nodule in greatest transverse diameter); no increase in size of liver or spleen | Irrelevant if positive prior to therapy; cell type should be specified |
| SD | Failure to attain CR/PR or PD | a) FDG-avid or PET positive prior to therapy; PET positive at prior sites of disease and no new sites on CT or PET b) Variable FDG- | | |

TABLE 4-continued

| | | | Spleen, | Bone |
|---|---|---|---|---|
| Response | Definition | Nodal masses | liver | marrow |
| | | avid or PET negative; no change in size of previous lesions on CT | | |
| Relapsed disease or PD | Any new lesion or increase by ≥ 50% of previously involved sites from nadir | Appearance of a new lesion(s) > 1.5 cm in any axis, ≥ 50% increase in SPD of more than one node, or ≥ 50% increase in longest diameter of a previously identified node ≥ 1 cm in short axis Lesions PET positive if FDG-avid lymphoma or PET positive prior to therapy | > 50% increase from nadir in the SPD of any previous lesions | New or recurrent involvement |

Abbreviations: CR, complete remission;
FDG, [$^{18}$F]fluorodeoxyglucose;
PET, positron emission tomography;
CT, computed tomography;
PR, partial remission;
SPD, sum of the product of the diameters;
SD, stable disease;
PD, progressive disease DCR (CR+PR+SD) was considered the most relevant efficacy endpoint the analysis of patient characteristic and biomarkers in this trial as the majority of patients with SD had marked target lesion reduction but as per study design were not treated beyond cycle 3. Accordingly, patients having SD included in the analysis.

At least the following characteristics of patients were evaluated to determine if there existed a correlation between the characteristic and the observed DCR of patients treated with the anti-CD19 antibody: a) age, b) gender, c) if patients had received a dose of Rituximab within the last 6 months, d) whether the patients were Rituximab refractory, e) whether patients have the FCgammaRIIIa high or low affinity allele, f) whether patients have the FCgammaRIIa high or low affinity allele, g) whether patients had a duration of response to the previous treatment of greater than 12 months, h) baseline peripheral T cell counts (cells/µl), i) baseline peripheral NK cell count (cells/µl) and j) baseline CD16 expression on peripheral NK cells (Antibodies Bound per Cells—ABCs).

Example 1 and Example 2 above were used to evaluate the baseline peripheral NK cell counts, T cell counts and baseline CD16 expression on peripheral NK cells. The data is shown in Table 2.

A Receiver Operating Characteristic (ROC) analysis was used to analyse the predictivity, specifity and sensitivity and to determine the cut offs for the potential biomarkers of NK cell count, T cell count and CD16 expression (ABCs) on peripheral NK cells. A ROC plot displays the performance of a binary classification method with continuous or discrete ordinal output. It shows the sensitivity (the proportion of correctly classified positive observations) and specificity (the proportion of correctly classified negative observations) as the output threshold is moved over the range of all possible values. See Swets J A: The Relative Operating Characteristic in Psychology. Science 1973, 182: 990-1000, and Pepe M S: The statistical evaluation of medical tests for classification and prediction. Oxford: Oxford University Press; 2003. In the ROC context, the area under the curve (AUC) measures the performance of a classifier and is frequently applied for method comparison. A higher AUC means a better classification. The AUC for peripheral NK/T cell counts and for CD16 expression on NK cells is 0.66, 0.53 and 0.61 respectively (FIGS. 3, 4 and 5).

In general the determination of the cut off depends on the objective the respective method is directed to. Various criteria such as maximum accuracy, maximum diagnostic odds ratio, minimal error rate, maximum sensitivity and/or maximum specificity would lead to a different determination of the cut off. In addition a balance between more of such criteria, e.g. sensitivity and specificity would also lead to a specific determination of the cut off.

Therefore several methods or criteria for selecting optimal cutoffs exist, including methods maximizing accuracy, sensitivity+specificity, predictive values, diagnostic likelihood ratios or prevalence. Due to the asymmetry of the CD16 expression-ROC curve (See FIG. 4) the majority of methods result in a cut off of 60,000 ABC (the points with the greatest distance between ROC curve and the bisecting line) whereas, the symmetry of the NK cell count ROC curve (See FIG. 3) explains why different values for the best cut off could be obtained when applying different methods. In this particular study, for both biomarkers more weight was assigned to sensitivity and, therefore, 100 NK cells/µl and a CD16 expression level of 60,000 ABCs, respectively, were chosen as cut offs to analyze the DCR and PFS within the subgroups. For peripheral T cell counts, the AUC is 0.53 and the ROC curve is close to the bisectrix at any value of specificity and sensitivity therefore even selecting a different cut off than 500 cell//µl had no impact on the negative results of the DCR and PFS subgroup analysis.

The determination of the cut off can be balanced either in favor of sensitivity or specificity. If even more weight is assigned to sensitivity for the identification of the optimal cut-off the method would be different and a lower cut-off for the NK cell count is contemplated. In such case a cut off of at least 50 NK cells/µl is determined. Alternatively, a cut off of at least 60 NK cells/µl, at least 70 NK cells/µl, at least 80 NK cells/µl, at least 90 NK cells/µl or at least 100 NK cells/µl is determined.

For maximizing the specificity of the disclosed method the cut-off for the NK cell count is increased and is determined between at least 100 NK cells/µl up to at least 150 NK cells/µl. Therefore for maximizing the specificity a cut off of at least 100 NK cells/µl, at least 110 NK cells/µl, at least 120 NK cells/µl, at least 130 NK cells/µl, at least 140 NK cells/µl or at least 150 NK cells/µl is selected.

The cut off values determined in this particular study (100 NK cells/µl and a CD16 expression level of 60,000 ABCs) were used for the following statistical analysis.

Forest plots were used to analyze all patient characteristics and biomarkers in order to determine the correlation of the individual characteristic with DCR. The results are shown in FIG. 7. Based upon the Forest Plot analysis of the different patient characteristics and their correlation to DCR, in DLBCL and iNHL patients the following characteristics showed statistically significant differences: 1) baseline peripheral NK cell count of at least 100 cells/µl and baseline expression of CD16 on peripheral NK cells of at least 60,000 ABCs ($\chi^2$ unadjusted p value=0.029/0.003) (FIG. 7).

In order to ensure that CD16 expression and NK cell count were independent characteristics, which did not influence on the other, a parametric and nonparametric correlation analysis was done. Data on CD16 expression and NK cell count was available for 51 patients. Pearson's r was 0.019 with a two-tailed p value=0.9 and Spearman's r was 0.036 with a two-tailed p value=0.8. The results are graphically presented in FIG. 6. In conclusion, CD16 expression and NK cell count at the determined thresholds are not correlated, therefore, they are considered fully independent predictors of the probability of a patient for benefiting from MOR00208 treatment.

The following characteristics were not found to be predictive of DCR: a) age, b) gender, c) if patients had received a dose of Rituximab within the last 6 months, d) whether the patients were Rituximab refractory, e) whether patients have the FCgammaRIIIa high or low affinity allele, f) whether patients have the FCgammaRIIa high or low affinity allele, g) whether patients had a duration of response to the treatment of greater than 12 months, or h) baseline peripheral T cell counts. See FIG. 7.

Both 1) baseline peripheral NK cell counts and 2) baseline CD16 expression on peripheral NK cells showed clear correlations to patient response with MOR00208 therapy. Specifically, patients having a baseline NK cell count of at least 100 cells/μl correlated with a higher Disease Control Rate (DCR). DCR includes patients have Complete Response (CR)+Partial Response (PR)+Stable Disease (SD). In addition, patients having a baseline CD16 expression on peripheral NK cells of at least 60,000 ABCs correlated with higher Disease Control Rate (DCR).

Progression Free Survival (PFS) is the length of time during and after the treatment of a disease that a patient lives with the disease but it does not get worse. This is an additional important endpoint of a clinical trial, and an indicator of effectiveness in patients. PFS was compared within the following patient characteristics: a) baseline peripheral NK cell count of at least 100 cells/μl or less, b) baseline CD16 expression on peripheral NK cells of at least 60,000 ABCs or less, and c) baseline peripheral T cell count of at least 500 cells/μl or less. The results are shown in FIGS. 8-10. The PFS comparing patients having NK cell counts having at least 100 cells/μl as compared to patients having lower NK cell counts showed a statistically significant difference with a HR of 0.1561 (unadjusted log-rank p value=0.0003). This further confirms the predictivity of NK cells counts in the response of patients treated with MOR00208 of those patients having CLL, NHL, ALL or SLL.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

---

The invention claimed is:

1. A method for the treatment of a human subject having a non-Hodgkin's lymphoma, said method comprising:

identifying the human subject as having a peripheral natural killer (NK) cell count at baseline of at least 100 NK cells/µl in a blood sample obtained from the human subject; and administering an anti-CD19 antibody to the human subject, wherein the anti-CD19 antibody comprises an HCDR1 region comprising the sequence SYVMH (SEQ ID NO:1), an HCDR2 region comprising the sequence NPYNDG (SEQ ID NO:2), an HCDR3 region comprising the sequence GTYYYGTRVFDY (SEQ ID NO:3), an LCDR1 region comprising the sequence RSSKSLONVNGNTYLY (SEQ ID NO:4), an LCDR2 region comprising the sequence RMSNLNS (SEQ ID NO:5), and an LCDR3 region comprising the sequence MQHLEYPIT (SEQ ID NO:6).

2. The method according to claim 1, wherein the anti-CD19 antibody comprises a heavy chain variable region of the sequence

```
                                    (SEQ ID NO: 10)
EVQLVESGGGLVKPGGSLKLSCAASGYTFTSYVMHWVRQAPGKGLEWIG
YINPYNDGTKYNEKFQGRVTISSDKSISTAYMELSSLRSEDTAMYYCAR
GTYYYGTRVFDYWGQGTLVTVSS
and a light chain variable variable region of the
sequence
                                    (SEQ ID NO: 11)
DIVMTQSPATLSLSPGERATLSCRSSKSLQNVNGNTYLYWFQQKPGQSP
QLLIYRMSNLNSGVPDRFSGSGSGTEFTLTISSLEPEDFAVYYCMQHLE
YPITFGAGTKLEIK.
```

3. The method according to claim 1, wherein the anti-CD19 antibody comprises a heavy chain comprising the sequence

```
                                    (SEQ ID NO: 8)
EVQLVESGGGLVKPGGSLKLSCAASGYTFTSYVMHWVRQAPGKGLEWIG

YINPYNDGTKYNEKFQGRVTISSDKSISTAYMELSSLRSEDTAMYYCAR

GTYYYGTRVFDYWGQGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPDVF

LFPPKPKDTLMISRTPEVTCVVVDVSHEDPEVQFNWYVDGVEVHNAKTK

PREEQFNSTFRVVSVLTVVHQDWLNGKEYKCKVSNKALPAPEEKTISKT

KGQPREPQVYTLPPSREEMTKNQVSLTCLVKGFYPSDIAVEWESNGQPE

NNYKTTPPMLDSDGSFFLYSKLIVDKSRWQQGNVFSCSVMHEALHNHYT

QKSLSLSPGK
and a light chain comprising the sequence
                                    (SEQ ID NO: 9)
DIVMTQSPATLSLSPGERATLSCRSSKSLQNVNGNTYLYWFQQKPGQSP

QLLIYRMSNLNSGVPDRFSGSGSGTEFTLTISSLEPEDFAVYYCMQHLE

YPITFGAGTKLEIKRTVAAPSVFIFPPSDEQLKSGTASWCLLNNFYPRE

AKVQWKVDNALQSGNSQESVTEQDSKDSTYSLSSTLTLSKADYEKHKVY

ACEVTHQGLSSPVTKSFNRGEC.
```

4. The method according to claim 1, wherein the non-Hodgkin's lymphoma is follicular lymphoma.

5. The method according to claim 4, wherein the anti-CD19 antibody comprises a heavy chain variable region comprising the sequence set forth in SEQ ID NO:10 and a light chain variable region comprising the sequence set forth in SEQ ID NO:11.

6. The method according to claim 4, wherein the anti-CD19 antibody comprises a heavy chain comprising the sequence set forth in SEQ ID NO:8 and a light chain comprising the sequence set forth in SEQ ID NO:9.

7. The method according to claim 1, wherein the non-Hodgkin's lymphoma is small lymphocytic lymphoma.

8. The method according to claim 7, wherein the anti-CD19 antibody comprises a heavy chain variable region comprising the sequence set forth in SEQ ID NO:10 and a light chain variable region comprising the sequence set forth in SEQ ID NO:11.

9. The method according to claim 7, wherein the anti-CD19 antibody comprises a heavy chain comprising the sequence set forth in SEQ ID NO:8 and a light chain comprising the sequence set forth in SEQ ID NO:9.

10. The method according to claim 1, wherein the non-Hodgkin's lymphoma is mucosa-associated lymphoid tissue lymphoma.

11. The method according to claim 10, wherein the anti-CD19 antibody comprises a heavy chain variable region comprising the sequence set forth in SEQ ID NO:10 and a light chain variable region comprising the sequence set forth in SEQ ID NO:11.

12. The method according to claim 10, wherein the anti-CD19 antibody comprises a heavy chain comprising the sequence set forth in SEQ ID NO:8 and a light chain comprising the sequence set forth in SEQ ID NO:9.

13. The method according to claim 1, wherein the non-Hodgkin's lymphoma is marginal zone lymphoma.

14. The method according to claim 13, wherein the anti-CD19 antibody comprises a heavy chain variable region comprising the sequence set forth in SEQ ID NO:10 and a light chain variable region comprising the sequence set forth in SEQ ID NO:11.

15. The method according to claim 13, wherein the anti-CD19 antibody comprises a heavy chain comprising the sequence set forth in SEQ ID NO:8 and a light chain comprising the sequence set forth in SEQ ID NO:9.

16. The method according to claim 1, wherein the non-Hodgkin's lymphoma is diffuse large B cell lymphoma.

17. The method according to claim 16, wherein the anti-CD19 antibody comprises a heavy chain variable region comprising the sequence set forth in SEQ ID NO:10 and a light chain variable region comprising the sequence set forth in SEQ ID NO:11.

18. The method according to claim 16, wherein the anti-CD19 antibody comprises a heavy chain comprising the sequence set forth in SEQ ID NO:8 and a light chain comprising the sequence set forth in SEQ ID NO:9.

19. The method according to claim 1, wherein the non-Hodgkin's lymphoma is Burkitt's lymphoma.

20. The method according to claim 19, wherein the anti-CD19 antibody comprises a heavy chain variable region comprising the sequence set forth in SEQ ID NO: 10 and a light chain variable region comprising the sequence set forth in SEQ ID NO:11.

21. The method according to claim 19, wherein the anti-CD19 antibody comprises a heavy chain comprising the sequence set forth in SEQ ID NO:8 and a light chain comprising the sequence set forth in SEQ ID NO:9.

22. The method according to claim 1, wherein the non-Hodgkin's lymphoma is mantle cell lymphoma.

23. The method according to claim 22, wherein the anti-CD19 antibody comprises a heavy chain variable region comprising the sequence set forth in SEQ ID NO: 10 and a light chain variable region comprising the sequence set forth in SEQ ID NO:11.

24. The method according to claim 22, wherein the anti-CD19 antibody comprises a heavy chain comprising the sequence set forth in SEQ ID NO:8 and a light chain comprising the sequence set forth in SEQ ID NO:9.

* * * * *